(12) United States Patent
Otani et al.

(10) Patent No.: US 10,519,419 B2
(45) Date of Patent: Dec. 31, 2019

(54) METHOD FOR PRODUCING CULTURE MEDIUM COMPOSITION

(71) Applicant: NISSAN CHEMICAL CORPORATION, Tokyo (JP)

(72) Inventors: Misayo Otani, Funabashi (JP); Koichiro Saruhashi, Funabashi (JP); Taito Nishino, Shiraoka (JP); Ayako Aihara, Shiraoka (JP); Hisashi Ishii, Saitama (JP); Keigo Matsumoto, Funabashi (JP)

(73) Assignee: NISSAN CHEMICAL CORPORATION, Tokyo (JP)

(*) Notice: Subject to any disclaimer, the term of this patent is extended or adjusted under 35 U.S.C. 154(b) by 0 days.

(21) Appl. No.: 15/113,753

(22) PCT Filed: Jan. 23, 2015

(86) PCT No.: PCT/JP2015/051786
§ 371 (c)(1),
(2) Date: Jul. 22, 2016

(87) PCT Pub. No.: WO2015/111685
PCT Pub. Date: Jul. 30, 2015

(65) Prior Publication Data
US 2017/0002311 A1  Jan. 5, 2017

(30) Foreign Application Priority Data

Jan. 23, 2014  (JP) .................................. 2014-010841
Aug. 25, 2014  (JP) .................................. 2014-170992

(51) Int. Cl.
C12N 5/00 (2006.01)
C08B 37/00 (2006.01)

(52) U.S. Cl.
CPC .......... *C12N 5/0018* (2013.01); *C08B 37/006* (2013.01); *C12N 5/0025* (2013.01); *C12N 2500/34* (2013.01)

(58) Field of Classification Search
None
See application file for complete search history.

(56) References Cited

U.S. PATENT DOCUMENTS

| 5,017,491 | A | * | 5/1991 | Freyssinet | ................ | A01H 5/10 |
| | | | | | | 435/428 |
| 5,549,921 | A | * | 8/1996 | Robinson | ............. | A01K 97/045 |
| | | | | | | 426/512 |
| 5,596,084 | A | * | 1/1997 | Sanderson | ................ | C08L 5/00 |
| | | | | | | 536/3 |
| 6,451,772 | B1 | * | 9/2002 | Bousman | ............. | A61K 9/0019 |
| | | | | | | 424/282.1 |
| 2008/0145505 | A1 | | 6/2008 | Bezanson et al. | | |
| 2008/0213285 | A1 | * | 9/2008 | Subtil-Sands | ........ | C07K 14/295 |
| | | | | | | 424/164.1 |
| 2011/0008470 | A1 | * | 1/2011 | Trudsoe | .................... | A61K 8/73 |
| | | | | | | 424/722 |
| 2011/0130473 | A1 | * | 6/2011 | Fuchs | ................. | C08B 37/0003 |
| | | | | | | 514/777 |
| 2011/0177567 | A1 | * | 7/2011 | Bakker | ................... | C12M 41/26 |
| | | | | | | 435/110 |
| 2011/0268843 | A1 | | 11/2011 | Wu et al. | | |
| 2011/0281307 | A1 | | 11/2011 | Yang et al. | | |
| 2014/0106348 | A1 | | 4/2014 | Nishino et al. | | |

FOREIGN PATENT DOCUMENTS

| CN | 103113488 A | 5/2013 |
| JP | H08-140673 A | 6/1996 |
| JP | 2010-512750 A | 4/2010 |
| JP | 2012-532236 A | 12/2012 |
| WO | WO 2014/017513 A1 | 1/2014 |

OTHER PUBLICATIONS

Doner et al. Carbohydrate Res. (1995) 273: 225-233 (Year: 1995).*
Definition of turbid downloaded from http://www.thefredictionary.com/turbid on 112/31/2017 (Year: 2017).*
http://thedifferencebetween.com/differenece-between-hydronium-ion-and-vs-hydrogen-ion downloaded Jan. 1, 2018 (Year: 2018).*
Camelin et al. Biotechnol. Progress (1993) 9: 291-297 (Year: 1993).*
Machine translation of CN 102113488, published on May 22, 2013) downloaded from Espacenet on Aug. 10, 2019 (Year: 2013).*
Chemical Abstracts Plus, CAPLUS Accession No. 2013:797357, entry for Chang et al., "Easily dispersed and dissolved transparent type low acyl gellan gum extraction method," Chinese Patent Application 103113488 A (published May 22, 2013).
Horikawa et al., "Novel 3D Cell Culture Media 'FCeM Series' for Anticancer Drug Screening," *Bio. Industry*, 31(1): 65-71 (2014).
Otsuji et al., "A 3D Sphere Culture System Containing Functional Polymers for Large-Scale Human Pluripotent Stem Cell Production," *Stem Cell Reports*, 2: 734-745 (2014).

(Continued)

*Primary Examiner* — Susan M Hanley
(74) *Attorney, Agent, or Firm* — Leydig, Voit & Mayer, Ltd.

(57) ABSTRACT

The present invention provides a production method of a medium composition, including previously removing divalent metal cations contained in a polymer compound having an anionic functional group, preparing a dry powder of the polymer compound, and mixing the dry powder and the medium, and the like. The present invention also provides a purification method of a polymer compound having an anionic functional group, which includes mixing a suspension of the polymer compound having an anionic functional group in water and a cation exchanger that exchanges a divalent metal cation with a monovalent metal cation to give a polymer compound having an anionic functional group, which shows a reduced amount of contaminating divalent metal cations.

13 Claims, 6 Drawing Sheets

(56) References Cited

OTHER PUBLICATIONS

Japan Patent Office, International Search Report in International Patent Application No. PCT/JP2015/051786 (dated Apr. 14, 2015).
Bajaj et al., "Gellan Gum: Fermentative Production, Downstream Processing and Applications," *Food Technol. Biotechnol.*, 45(4): 341-354 (2007).
European Patent Office, Extended European Search Report in European Patent Application No. 15740061.5 (dated Sep. 22, 2017).

* cited by examiner with deacylated gellan gum | without deacylated gellan gum xanthan gum　　　κ-carageenan + locust bean gum
(0.15%)　　　　　(0.05%)　　+　　(0.05%)

HepG2 cell sphere laminin-coated GEM alginic acid beads collagen gel capsule suspension culture of
rice-derived callus

METHOD FOR PRODUCING CULTURE MEDIUM COMPOSITION

CROSS-REFERENCE TO RELATED APPLICATIONS

This patent application is the U.S. national phase of International Patent Application No. PCT/JP2015/051786, filed on Jan. 23, 2015, which claims the benefit of Japanese Patent Application No. 2014-010841, filed Jan. 23, 2014, and Japanese Patent Application No. 2014-170992, filed Aug. 25, 2014, the disclosures of which are incorporated herein by reference in their entireties for all purposes.

TECHNICAL FIELD

The present invention relates to a production method of a medium composition for culturing animal and plant cells and/or tissues particularly in a three dimensional or suspended state by using a polymer compound having an anionic functional group and showing improved solubility in water.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture. Cell culture is a technique for proliferating, differentiating or maintaining separated cells in vitro in a medium, and is indispensable for detailed analyses of the in vivo function and structure of various organs, tissues and cells. In addition, the cells and/or tissues cultured by the technique are utilized in various fields for efficacy and toxicity evaluation of chemical substances, pharmaceutical products and the like, large-scale production of useful substances such as enzymes, cell growth factors, antibodies and the like, regenerative medicine supplementing organ, tissue and cell that were lost by disease and deficiency, improvement of plant brand, production of genetically modified products, and the like.

Animal-derived cells are broadly divided into non-adherent cells and adherent cells based on the properties thereof. Non-adherent cells are cells that do not require a scaffold for growth and proliferation, and adherent cells are cells that require a scaffold for growth and proliferation. Most of the cells constituting the living body are the latter, adherent cells. As culture methods of adherent cells, single layer culture, dispersion culture, embedded culture, microcarrier culture, sphere culture and the like are known.

Single layer culture is a method of cultivating the object cell as a single layer by using, as a scaffold, a culture container made of glass or a synthetic polymer material that underwent various surface treatments, or supportive cells called feeder cells, and is most generally prevalent. For example, culture methods using culture containers of various shapes or properties such as polystyrene applied with various surface treatments (plasma treatment, corona treatment etc.), coated with cell adhesion factors such as collagen, fibronectin, polylysine and the like, or plated with feeder cells in advance and the like have been developed. However, the single layer culture is problematic in that cells cannot maintain the specific functions they have in vivo for a long term, since the two-dimensional culture environment thereof is completely different from the in vivo environment, the cells cannot reconstruct a tissue similar to that in vivo, it is not suitable for a mass culture of cells since the cell number per a constant area is limited, and the like (patent document 1). In addition, a method of cultivating the object cell on feeder cells sometimes faces a problem in separation of the object cells from the feeder cells (non-patent document 1).

Dispersion culture is a method of cultivating adherent cells in a suspended state, which includes seeding the cells in a medium, and stirring the culture medium in a culture container applied with a surface treatment for inhibiting cell adhesion, to inhibit attachment of the cells to the culture container. However, the adherent cells cultured by the method cannot adhere to a scaffold, and therefore, the method cannot be applied to a cell that essentially requires adhesion to a scaffold for cell proliferation. In addition, being constantly disrupted by a shear force, the cell cannot exhibit its inherent cell function, and therefore, functional cells sometimes cannot be cultivated in a large amount (non-patent document 2).

Embedded culture is a method of cultivating cells by embedding and fixing the cells in a solid or semisolid gel substrate such as agar, methylcellulose, collagen gel, gelatin, fibrin, agarose, alginates and the like. Since the method enables three-dimensional cultivation of the cells in a state closer to in vivo and the gel substrate itself sometimes promotes proliferation and differentiation of the cells, the cells can be cultivated at high density while maintaining the function of the cell, as compared to single layer culture and dispersion culture (patent documents 2, 3). Furthermore, a method of cultivating cells, including forming a microcapsule with a size of 100-300 μm by embedding the cells in the gel substrate, and cultivating the cells in an aqueous solution medium while dispersing the microcapsule has also been developed (non-patent document 3). However, these methods have problems in that successive observation of cultured cells is not possible unless a visible light permeates the gel substrate, recovery of cells from the medium requires a complicated operation that damages the cells such as an enzyme treatment (e.g., collagenase treatment in the case of collagen gel) and the like, since the medium and microcapsule containing a gel substrate have high viscosity, medium exchange necessary for long-term cultivation is difficult and the like. In recent years, techniques enabling cell recovery from a gel substrate by a treatment with heat, shear force and the like have been developed. However, the heat, shear force and the like may exert an adverse effect on the cell function, and the safety of the gel substrate for the living body has not been clarified yet (patent documents 4, 5, non-patent documents 4, 5, 6, 7). In addition, a sol food for preventing precipitation and floating of a particulate food such as fruit, vegetable and the like cut small to keep the food uniformly dispersed and suspended has been developed in the food field. However, the sol food does not consider recovery of the dispersed particulate food, and whether the cells and tissues can be subjected to suspension culture has not been examined (patent document 6).

Microcarrier culture is a method of cultivating cells in a suspended state by proliferating cells in a single layer on the surface of a fine particle slightly heavier than water (hereinafter to be also referred to as a microcarrier), and stirring the fine particles in a culture container such as a flask and the like. Generally, the microcarrier used for the method is a spherical particle having diameter 100-300 μm, surface area 3000-6000 $cm^2/g$, specific gravity 1.03-1.05, and is composed of a material such as dextran, gelatin, alginic acid, polystyrene and the like. Collagen, gelatin, or a charged group such as dimethylaminoethyl and the like may also be provided to the surface of a microcarrier to facilitate attachment of the cell. This method is applied to a mass culture of a cell since it can markedly increase the culture area (patent documents 7, 8). However, it is difficult to attach the object cell almost uniformly to all microcarriers, and problems occur such as detachment of the cells from the microcarrier due to a shear force during stirring, damage on the cells and the like (non-patent document 8).

Sphere culture is a culture method including forming an aggregate composed of several dozen-several hundred object cells (hereinafter to be also referred to as a sphere), and culturing the aggregates with standing or shaking in a medium. It is known that a sphere has a high cell density, reconstructs cell-cell interactions and cell structure close to those in the in vivo environment, and can be cultured while maintaining the cell function for a longer term as compared to a single layer culture and a dispersion culture method (non-patent documents 9, 10). However, the sphere culture cannot form a large sphere, since supply of nutrition inside the sphere and discharge of wastes are difficult when the size of the sphere is too large. In addition, since the formed sphere needs to be cultivated in a dispersed state on the bottom of a culture container, the number of spheres per a given volume cannot be increased with ease, and it is not suitable for a mass culture. Furthermore, as a method of forming a sphere, hanging drop culture, culture on cell non-adhesive surface, culture inside microwell, rotation culture, culture utilizing cell scaffold, coagulation by centrifugal force, ultrasonication, electric field or magnetic field and the like are known. However, these methods are problematic in that the operation is complicated, recovery of sphere is difficult, size control and large-scale production are difficult, influence on the cell is unknown, special exclusive container and apparatus are necessary and the like (patent document 9).

On the other hand, as for plants, cell, protoplast without a cell wall or organ, tissue, callus of plant such as leaf, stalk, root, growing point, seed, embryo, pollen and the like can also be grown by culture in an aseptic state. Using a culture technique for such plant tissues and cells, brand improvement of plant and production of useful substances have been made possible. As a method for proliferating plant cells and tissues in a large amount in a short time, a method of suspension cultivation of plant cells and tissues in a liquid medium is known (non-patent document 11). To achieve good proliferation thereof, supply of sufficient oxygen, maintenance of a uniform mixing state, prevention of cell damage and the like are important. The oxygen supply to a culture medium and suspending of cells and tissues may be performed by combining aeration and mechanical stirring, or aeration alone. The former may result in defective proliferation due to a damage on the cells and tissues by stirring, and the latter is problematic in that, even though shearing of cells and tissues is less, since a uniform mixing state may be difficult to maintain in high density culture, the cells and tissues form sediment to lower the proliferation efficiency and the like.

DOCUMENT LIST

Patent Document patent document 1: JP-A-2001-128660
patent document 2: JP-A-S62-171680
patent document 3: JP-A-S63-209581
patent document 4: JP-A-2009-29967
patent document 5: JP-A-2005-60570
patent document 6: JP-A-8-23893
patent document 7: JP-A-2004-236553
patent document 8: WO 2010/059775
patent document 9: JP-A-2012-65555

Non-Patent Document non-patent document 1: Klimanskaya et al., Lancet 2005, 365:1636-1641
non-patent document 2: King et al., Curr Opin Chem Biol. 2007, 11:394-398
non-patent document 3: Murua et al., J. of Controlled Release 2008, 132:76-83
non-patent document 4: Mendes, Chemical Society Reviews 2008, 37:2512-2529
non-patent document 5: Moon et al., Chemical Society Reviews 2012, 41:4860-4883
non-patent document 6: Pek et al., Nature Nanotechnol. 2008, 3:671-675
non-patent document 7: Liu et al., Soft Matter 2011, 7:5430-5436
non-patent document 8: Leung et al., Tissue Engineering 2011, 17:165-172
non-patent document 9: Stahl et al., Biochem. Biophys. Res. Comm. 2004, 322:684-692
non-patent document 10: Lin et al., Biotechnol J. 2008, 3:1172-1184
non-patent document 11: Weathers et al., Appl Microbiol Biotechnol 2010, 85:1339-1351

SUMMARY OF THE INVENTION

Problems to be Solved by the Invention

The present inventors have conducted intensive studies in an attempt to solve the aforementioned problems and found that suspension culture of animal and plant cells and/or tissues can be performed while keeping them still by mixing a structure comprising a polymer compound having an anionic functional group, such as deacylated gellan gum and the like, in a liquid medium, without substantially increasing the viscosity of the liquid medium, and that the growth activity of the cell is promoted by culture using this medium composition.

During the process of development of the medium composition, a new problem was found that a polymer compound having an anionic functional group, such as deacylated gellan gum and the like, has low solubility in water, and a polymer compound having an anionic functional group needs to be dissolved in an aqueous solvent under high temperature conditions and the like to give a desired medium composition.

Accordingly, it is an object of the present invention to provide a production method of a medium composition that increases solubility of the above-mentioned polymer compound having an anionic functional group in water, and more simplifies mixing and dissolution of the aforementioned compound in the medium, and the like.

Means of Solving the Problems

The present inventors have conducted intensive studies in an attempt to solve the aforementioned problems and found that a divalent metal cation mixed in a trace amount in a polymer compound having an anionic functional group decreases solubility in water. They have also found that a powder obtained by drying the polymer compound is dissolved in water at room temperature or cold water by previously removing the divalent metal cation mixed therein by a treatment with a chelating agent or ion exchange resin, and that cells and/or tissues can be uniformly dispersed in a suspended state by mixing the thus-obtained aqueous solution with a liquid medium, without substantially increasing the viscosity of the liquid medium, which resulted in the completion of the present invention.

That is, the present invention is as follows:

(1) A method of producing a medium composition capable of suspension culture of cells or tissues, comprising mixing a polymer compound having an anionic functional group, which is substantially free of a divalent metal cation, and a medium.

(2) A method of producing a medium composition capable of suspension culture of cells or tissues, comprising subjecting a polymer compound having an anionic functional group to a divalent metal cation removal treatment to give a polymer compound having an anionic functional group, which shows a reduced amount of contaminating divalent metal cations, and mixing the polymer compound and a medium.

(3) The production method of (2), wherein the divalent metal cation removal treatment is performed using a chelating agent or a cation exchanger.

(4) The production method of (2), wherein the divalent metal cation removal treatment is performed by mixing a suspension of the polymer compound having an anionic functional group in water and a cation exchanger.

(5) The production method of (4), wherein the suspension of the polymer compound having an anionic functional group in water is mixed with the cation exchanger at 10-70° C.

(6) The production method of any of (1)-(5), wherein the aforementioned divalent metal cation is at least one kind selected from the group consisting of calcium ion, magnesium ion, zinc ion, iron ion and copper ion.

(7) The production method of any of (1)-(6), wherein the polymer compound is deacylated gellan gum or a salt thereof.

(8) The production method of any of (1)-(7), comprising mixing an aqueous solution of the aforementioned polymer compound and an aqueous solution of the medium.

(9) The production method of (8), wherein each aqueous solution is sterilized by filtration before mixing.

(10) The production method of (8), wherein the aqueous solution of the aforementioned polymer compound is sterilized in an autoclave.

(11) The production method of (8), wherein the aqueous solution of the aforementioned polymer compound and the aqueous solution of the medium are mixed with stirring.

(12) The production method of (8), comprising mixing with stirring in a homomixer.

(13) The production method of (3), wherein the chelating agent is ethylenediaminetetraacetic acid.

(14) The production method of (3), wherein the cation exchanger is of a sodium type.

(15) A medium additive for preparing a medium composition capable of suspension culture of cells or tissues, comprising
a polymer compound having an anionic functional group, which is substantially free of a divalent metal cation(s) and is sterilized.

(16) The medium additive of (15), which is an aqueous solution.

(17) The medium additive of (15), wherein the aforementioned polymer compound having an anionic functional group is deacylated gellan gum or a salt thereof.

(18) A method of producing a medium additive for preparing a medium composition capable of suspension culture of cells or tissues, comprising
subjecting a polymer compound having an anionic functional group to a divalent metal cation removal treatment to give a polymer compound having an anionic functional group, which shows a reduced amount of contaminating divalent metal cations, and drying the polymer compound by spray dry or freeze-dry.

(19) The production method of (18), wherein the aforementioned polymer compound having an anionic functional group is deacylated gellan gum or a salt thereof.

(20) A purification method of a polymer compound having an anionic functional group, comprising
mixing a suspension of the polymer compound having an anionic functional group in water and a cation exchanger that exchanges a divalent metal cation with a monovalent metal cation to give a polymer compound having an anionic functional group, which shows a reduced amount of contaminating divalent metal cations.

(21) The purification method of (20), wherein the aforementioned cation exchanger is of a sodium type.

(22) The purification method of (20) or (21), wherein the suspension of the polymer compound having an anionic functional group in water is mixed with the aforementioned cation exchanger at 10-70° C.

(23) The purification method of any of (20)-(22), wherein the aforementioned divalent metal cation is at least one kind selected from the group consisting of calcium ion, magnesium ion, zinc ion, iron ion and copper ion.

(24) The purification method of any of (20)-(23), wherein the polymer compound is deacylated gellan gum or a salt thereof.

(25) The purification method of any of (20)-(24), wherein the suspension has a content of the polymer compound having an anionic functional group of 0.5-2.0% (w/v).

Effect of the Invention

The present invention provides a production method of a medium composition comprising mixing a powder obtained by drying a polymer compound having an anionic functional group, which shows improved solubility in water by removing a divalent metal cation(s), and a medium, and the like. Using the production method of the present invention, a medium composition capable of uniformly dispersing cells and/or tissues in a suspended state without substantially increasing the viscosity of the liquid medium can be prepared conveniently without requiring a heat treatment such as an autoclave treatment and the like.

DESCRIPTION OF EMBODIMENTS

Figure 1:
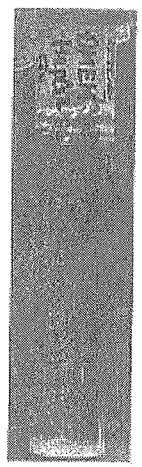
FIG. 1 is a Figure showing that, when spheres of HepG2 cells were cultured in the medium composition, the spheres were uniformly dispersed and could be cultured in a suspended state.

The present invention is explained in more detail in the following.

The terms used in the present specification are defined as follows.

The cell in the present invention is a most basic unit constituting animals and plants, which has, as its elements, cytoplasm and various organelles inside the cellular membrane. In this case, the nucleus encapsulating the DNA may or may not be contained intracellularly. For example, the animal-derived cells in the present invention include reproductive cells such as spermatozoon, oocyte and the like, somatic cells constituting the living body, stem cells, progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, nerve system cells, glial cells, neurons, oligodendrocytes, microglial, astrocytes, heart cells, esophagus cells, myocytes (e.g., smooth muscle cells or skeletal muscle cells), pancreatic beta cells, melanin cells, hematopoietic progenitor cells, mononuclear cells and the like. The somatic cells include cells collected from any tissue, for example, skin, kidney, spleen, adrenal gland, liver, lung, ovary, pancreas, uterus, stomach, colon, small intestine, large intestine, spleen, bladder, prostate, testis, thymus, muscle, connective tissue, bone, cartilage, blood vessel tissue, blood, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic reproductive stem cells, artificial pluripotent stem cells (iPS cell), neural stem cells, hematopoietic stem cells, mesenchymal stem cells, liver stem cells, pancreas stem cells, muscle stem cells, reproductive stem cells, intestinal stem cells, cancer stem cells, hair follicle stem cells and the like. Progenitor cells are cells on the way to differentiate from the aforementioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro, and examples thereof include, but are not limited to, CHO (Chinese hamster ovary cell line), HCT116, Huh7, HEK293 (human embryonic kidney cell), HeLa (human uterine cancer cell line), HepG2 (human liver cancer cell line), UT7/TPO (human leukemia cell line), MDCK, MDBK, BHK, C-33A, HT-29, AE-1, 3D9, Ns0/1, Jurkat, NIH3T3, PC12, S2, Sf9, Sf21, High Five (registered trade mark), Vero and the like.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, connective tissue, muscular tissue, nerve tissue and the like.

Examples of the plant tissue include meristem, epidermis tissue, assimilation tissue, mesophyll tissue, conductive tissue, mechanical tissue, parenchyma tissue, dedifferentiated cell cluster (callus) and the like.

When cells and/or tissues are cultivated, the cells and/or tissues to be cultivated can be selected freely from the cells and/or tissues described above and cultivated. The cells and/or tissues can be directly recovered from an animal or plant body. The cells and/or tissues may be induced, grown or transformed from an animal or plant body by applying a particular treatment and then collected. In this case, the treatment may be in vivo or in vitro. Examples of the animal include fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, *Macaca mulatta*, chimpanzee and human. The plant is not particularly limited as long as the collected cells and/or tissues can be applied to liquid culture. Examples thereof include, but are not limited to, plants (e.g., ginseng, periwinkle, henbane, coptis, belladonna etc.) producing crude drugs (e.g., saponin, alkaloids, berberine, scopolin, phytosterol etc.), plants (e.g., blueberry, safflower, madder, saffron etc.) producing dye or polysaccharide (e.g., anthocyanin, safflower dye, madder dye, saffron dye, flavones etc.) to be a starting material for cosmetic or food, or plants producing a pharmaceutical drug substance and the like.

Suspending of cells and/or tissues in the present invention refers to a state where cells and/or tissues do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like in the composition is referred to as "suspension standing", and cultivation of the cells and/or tissues in such condition is referred to as "suspension standing culture". In the "suspension standing", the period of suspending includes at least 5-60 min, 1 hr-24 hr, 1 day-21 days, though the period is not limited thereto as long as the suspended state is maintained.

A medium composition produced by the production method of the present invention is a composition containing a structure capable of culturing cells or tissues in a suspended state (preferably capable of suspension standing culture) and a medium.

The medium composition is preferably a composition permitting an exchange treatment of the medium composition during culture, and recovery of the cells or tissues after completion of the culture. More preferably, it is a medium composition that allows for recovery of the cells or tissues without any of a temperature change, a chemical treatment, an enzyme treatment and a shear force.

The "structure capable of suspension culture of cells or tissues" is formed from a particular compound and shows an effect of uniformly suspending cells and/or tissues. More particularly, it includes an assembly of polymer compounds via an ion, a three-dimensional network formed by polymer compounds and the like. It is known that polysaccharides form a microgel via a metal cation (e.g., JP-A-2004-129596), and the structure of the present invention also includes such microgel as one embodiment.

One embodiment of the assembly of polymer compounds via an ion is a film structure.

The size of the structure is preferably a size that passes a filter having a pore size of 0.2 μm to 200 μm when it is passed through a filter. The lower limit of the pore size is more preferably more than 1 μm and, in consideration of stable suspension of cells or tissues, it more preferably exceeds 5 μm. The upper limit of the pore size is more preferably less than 100 μm and, in consideration of the size of the cells or tissues, it is more preferably less than 70 μm.

The "particular compound" refers to a compound that forms, upon mixing with a liquid medium, an indeterminate structure which is uniformly dispersed in the liquid, substantially retains the cells and/or tissues without substantially increasing the viscosity of the liquid, and shows an effect of preventing sediment thereof. The "without substantially increasing the viscosity of the liquid" means that the viscosity of the liquid does not exceed 8 mPa·s. In this case, the viscosity of the liquid (that is, the viscosity of the medium composition to be produced by the production method of the present invention) is not more than 8 mPa·s, preferably not more than 4 mPa·s, more preferably not more than 2 mPa·s. Furthermore, the chemical structure, molecular weight, property etc. of the particular compound are not limited as long as it forms the structure in a liquid medium, and shows an effect of uniformly suspending (preferably suspension standing) the cells and/or tissues without substantially increasing the viscosity of the liquid.

The viscosity of the liquid containing the structure can be measured, for example, by the method described in the below-mentioned Examples. Specifically, it can be measured under 37° C. conditions and using an E-type viscosity meter (manufactured by Toki Sangyo Co., Ltd., TV-22 type viscosity meter, model: TVE-22L, corn roter: standard roter 1° 34'×R24, rotation number 100 rpm).

Examples of the "particular compound" include, but are not limited to, polymer compounds, preferably a polymer compound having an anionic functional group.

As the anionic functional group, carboxylic acid, sulfonic acid, phosphoric acid and a salt thereof can be mentioned, with preference given to carboxylic acid or a salt thereof.

As the polymer compound to be used in the present invention, one constituted of one or more kinds selected from the group consisting of the aforementioned anionic functional groups can be used.

Preferable specific examples of the polymer compound to be used in the present invention include, but are not limited to, polysaccharides wherein not less than 10 single saccharides (e.g., triose, tetrose, pentose, hexsauce, heptose etc.) are polymerized, more preferably, acidic polysaccharides having an anionic functional group. The acidic polysaccharide here is not particularly limited as long as it has an anionic functional group in the structure thereof, and includes, for example, polysaccharides having a uronic acid (e.g., glucuronic acid, iduronic acid, galacturonic acid, mannuronic acid), polysaccharides having sulfuric acid or phosphate in a part of the structure thereof, and polysaccharides having the both structures, and includes not only naturally-obtained polysaccharides but also polysaccharides produced by microorganisms, polysaccharides produced by genetic engineering, and polysaccharides artificially synthesized using an enzyme. More specifically, examples thereof include polymer compounds composed of one or more kinds selected from the group consisting of hyaluronic acid, gellan gum, deacylated gellan gum (DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate and a salt thereof.

Examples of the salt here include alkali metal salts such as lithium, sodium, potassium; alkaline earth metal salts such as calcium, barium, magnesium; salts such as aluminum, zinc, copper, iron and the like; ammonium salt; quarternary ammonium salts such as tetraethylammonium, tetrabutylammonium, methyltributylammonium, cetyl trimethylammonium, benzylmethylhexyldecylammonium, choline and the like; salts with organic amines such as pyridine, triethylamine, diisopropylamine, ethanolamine, diolamine, tromethamine, meglumine, procaine, chloroprocaine and the like; salts with amino acid such as glycine, alanine, valine and the like; and the like.

The weight average molecular weight of these polymer compounds or polysaccharides is preferably 10,000 to 50,000,000, more preferably 100,000 to 20,000,000, still more preferably 1,000,000 to 10,000,000. For example, the molecular weight can be measured based on pullulan by gel penetration chromatography (GPC).

In the present invention, plural kinds (preferably two kinds) of the above-mentioned polysaccharides can be used in combination. The kind of the combination of the polysaccharides is not particularly limited as long as the aforementioned structure is formed in a liquid medium, and the cells and/or tissues can be uniformly suspended (preferably suspension stood) without substantially increasing the viscosity of the liquid. Preferably, the combination includes at least DAG or a salt thereof. That is, a preferable combination of polysaccharides contains DAG or a salt thereof, and polysaccharides other than DAG and a salt thereof (e.g., xanthan gum, alginic acid, carageenan, diutan gum, methylcellulose, locust bean gum or a salt thereof). Examples of specific combination of polysaccharides include, but are not limited to, DAG and rhamsan gum, DAG and diutan gum, DAG and xanthan gum, DAG and carageenan, DAG and xanthan gum, DAG and locust bean gum, DAG and K-carageenan, DAG and sodium alginate, DAG and methylcellulose and the like.

More preferable specific examples of the "particular compound" include hyaluronic acid, deacylated gellan gum, diutan gum, carageenan and xanthan gum and a salt thereof. Most preferable examples include deacylated gellan gum and a salt thereof, since the viscosity of the medium composition can be made low and the cells or tissues can be easily recovered.

The deacylated gellan gum in the present invention is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein R1, R2 are each a hydrogen atom, and n is an integer of two or more. R1 may contain a glyceryl group, R2 may contain an acetyl group, and the content of the acetyl group and glyceryl group is preferably not more than 10%, more preferably not more than 1%.

The aforementioned structure takes various forms depending on the particular compound. In the case of deacylated gellan gum, it uptakes a metal cation (e.g., calcium ion) in a liquid medium when mixed with the liquid medium, forms an indeterminate structure via the metal cation, and suspends the cells and/or tissues. The viscosity of the medium composition of the present invention prepared from deacylated gellan gum is not more than 8 mPa·s, preferably not more than 4 mPa·s, and more preferably not more than 2 mPa·s for easy recovery of the cells or tissues.

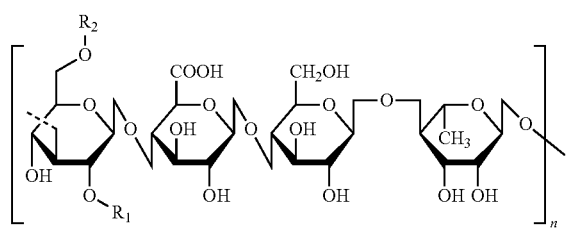

(I)

The "particular compound" can be obtained by a chemical synthesis method. When the compound is a naturally-occurring substance, it is preferably obtained from various plants, various animals, various microorganisms containing the compound by extraction, separation and purification by conventional techniques. For extraction, the compound can be extracted efficiently by using water and supercritical gas. For example, as a production method of gellan gum, a producing microorganism is cultured in a fermentation medium, a mucosal substance produced outside fungus is recovered by a general purification method and, after the steps of drying, pulverizing and the like, powderized. When it is deacylated gellan gum, an alkali treatment is applied when a mucous substance is recovered, the glyceryl group and the acetyl group bonded to 1-3 bonded glucose residue are deacylated and recovered. Examples of the purification method include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, and impurity can be removed and the compound can be purified by using them singly or in combination in any order, or repeatedly. Examples of the gellan gum-producing microorganism include, but are not limited to, Sphingomonas elodea and microorganisms obtained by altering the gene of Sphingomonas elodea.

When it is deacylated gellan gum, commercially available products, for example, "KELCOGEL (registered trade mark of CP Kelco) CG-LA" manufactured by SANSHO Co., Ltd., "KELCOGEL (registered trade mark of CP Kelco)" manufactured by San-Ei Gen F.F.I., Inc. and the like can be used.

The concentration of the particular compound in a medium is 0.0005% to 1.0% (weight/volume), preferably 0.001% to 0.4% (weight/volume), more preferably 0.005% to 0.1% (weight/volume), still more preferably 0.005% to 0.05% (weight/volume). For example, in the case of deacylated gellan gum, it is added to a medium at 0.001% to 1.0% (weight/volume), preferably 0.003% to 0.5% (weight/volume), more preferably 0.005% to 0.1% (weight/volume), more preferably 0.01% to 0.05% (weight/volume), most preferably, 0.01% to 0.02% (weight/volume). In the case of xanthan gum, it is added to a medium at 0.001% to 5.0% (weight/volume), preferably 0.01% to 1.0% (weight/volume), more preferably 0.05% to 0.5% (weight/volume), most preferably 0.1% to 0.2% (weight/volume). In the case of a K-carageenan and locust bean gum mixture, it is added to a medium at 0.001% to 5.0% (weight/volume), preferably 0.005% to 1.0% (weight/volume), more preferably 0.01% to 0.1% (weight/volume), most preferably 0.03% to 0.05% (weight/volume).

When plural kinds (preferably two kinds) of the above-mentioned polysaccharides are used in combination, the concentration of the polysaccharides can form the aforementioned structure in a liquid medium, and can uniformly suspend (preferably suspension stand) the cells and/or tissues without substantially increasing the viscosity of the liquid. For example, when a combination of DAG or a salt thereof and polysaccharide other than DAG and a salt thereof is used, the concentration of DAG or a salt thereof is, for example, 0.005-0.02% (weight/volume), preferably 0.01-0.02% (weight/volume), and the concentration of polysaccharide other than DAG and a salt thereof is, for example, 0.005-0.4% (weight/volume), preferably 0.1-0.4% (weight/volume). Specific examples of the combination of the concentration range include the following.

DAG or a salt thereof: 0.005-0.02% (preferably 0.01-0.02%) (weight/volume)

polysaccharide other than DAG xanthan gum: 0.1-0.4% (weight/volume)

sodium alginate: 0.1-0.4% (weight/volume) (preferably 0.0001-0.4% (weight/volume))

native gellan gum: 0.0001-0.4% (weight/volume)

locust bean gum: 0.1-0.4% (weight/volume)

methylcellulose: 0.1-0.4% (weight/volume) (preferably 0.2-0.4% (weight/volume))

carageenan: 0.05-0.1% (weight/volume)

diutan gum: 0.05-0.1% (weight/volume)

The concentration can be calculated by the following formula.

$$\text{Concentration (\%)} = \frac{\text{weight (g) of particular compound}}{\text{volume (ml) of medium composition}} \times 100$$

The aforementioned compound can also be further converted to a different derivative by a chemical synthesis method, and the thus-obtained derivative can also be used effectively in the present invention. Specifically, in the case of deacylated gellan gum, a derivative of a compound represented by the formula (I) wherein a hydroxyl group for R1 and/or R2 is substituted by C1-3 alkoxy group, C1-3 alkylsulfonyl group, a monosaccharide residue such as glucose, fructose and the like, oligosaccharide residue such as sucrose, lactose and the like, or amino acid residue such as glycine, arginine and the like can also be used in the present invention. In addition, the compound can also be crosslinked using a crosslinking agent such as 1-ethyl-3-(3-di-methyl-aminopropyl)carbodiimide (EDC) and the like.

The particular compound or a salt thereof to be used in the present invention can be present in any crystal form depending on the production conditions, and can be present as any hydrate. Such crystal form, hydrate and mixtures thereof are also encompassed in the scope of the present invention. In addition, they may be present as a solvate containing an organic solvent such as acetone, ethanol, tetrahydrofuran and the like. Such forms are all encompassed in the scope of the present invention.

The particular compound to be used in the present invention may be present in the form of tautomer formed by isomerization in the ring or outside the ring, geometric isomer or tautomer, or a mixture of geometric isomers, or mixtures thereof. When the compound of the present invention has an asymmetric center, irrespective of whether the compound is formed by isomerization, it may be present in the form of a resolved optical isomer or a mixture containing same at any ratio.

The medium composition of the present invention contains metal cation, for example, divalent metal cation (calcium ion, magnesium ion, zinc ion, iron ion and copper ion etc.), preferably calcium ion. In one embodiment, when a metal cation is contained polymer compounds having an anionic functional group gather via the metal cation; the polymer compounds having an anionic functional group form a tertiary network; or the polymer compounds having an anionic functional group form a microgel via the metal cation, whereby a structure capable of suspension culture of cells or tissues can be formed.

A medium composition produced by the production method of the present invention may contain the below-mentioned extracellular matrix, adhesion molecule and the like.

The present invention also includes a culture method for proliferating cells or tissues by using the medium composition, a method of recovering the obtained cells or tissues by, for example, filtration, centrifugation or magnetic separation, and a production method of a sphere by using the medium composition.

When cells and/or tissues are cultured in vitro, a structure composed of the particular compound to be used in the present invention shows an effect of suspending (preferably effect of suspension standing) the cells and/or tissues in a liquid containing the structure of the particular compound. By the suspending effect, a more increased amount of the cells and/or tissues per a given volume can be cultivated as compared to a single layer culture. When a conventional suspension culture method accompanies rotation or shaking operation, the proliferation rate and recovery rate of the cells and/or tissues may become low, or the function of the cell may be impaired since a shear force acts on the cells and/or tissues. Using the medium composition of the present invention, which contains a structure of the particular compound, can uniformly disperse the cells and/or tissues without an operation such as shaking and the like, and can obtain the object cells and/or tissues easily in a large amount without loss of the cell function. In addition, when cells and/or tissues are suspension cultured in a conventional medium containing a gel substrate, observation and recovery of the cells and/or tissues are sometimes difficult, and the function thereof is sometimes impaired during recovery. However, using the medium composition containing the structure of the particular compound of the present invention, the cells and/or tissues can be subjected to suspension culture, observed without impairment of the function thereof, and can be recovered. In addition, a conventional medium containing a gel substrate sometimes shows high viscosity that makes it difficult to exchange the medium. However, since the medium composition containing the structure of the particular compound of the present invention has low viscosity, it can be exchanged easily with a pipette, pump and the like.

The human-derived cells and/or tissues cultured by the method of the present invention can be transplanted for a treatment object to patients having a disease or disorder. In this case, treatment target disease, the kind of disorder, a pre-treatment method and a cell transplantation method are appropriately selected by those of ordinary skill in the art. The engraftment of the transplanted cells in the recipient, recovery from the disease or disorder, the presence or absence of side effects associated with transplantation, and treatment effect are appropriately examined and judged by general methods for transplantation therapy.

Since cells and/or tissues are grown efficiently, moreover, a medium composition produced by the production method of the present invention can be used as a reagent for the study of cells. For example, when a factor controlling the differentiation and proliferation of cells and tissues is to be elucidated, cells and the object factor are cocultured, and the number and kind of the cell, and changes in the cell surface differentiation marker and expressed gene are analyzed. In this case, using the medium composition of the present invention, the number of the analysis target cells can be efficiently amplified, and efficiently recovered as well. When the object factor is elucidated, the culture conditions, culture apparatus, the kind of medium, the kind of the compound of the present invention, the content of the particular compound, the kind of the additive, the content of the additive, culture period, culture temperature and the like are appropriately selected by those of ordinary skill in the art from the range described in the present specification. The cell that was proliferated or emerged by culture can be observed using a standard microscope in the pertinent field. In this case, cultured cells may be stained with a specific antibody. The expressed gene that has changed due to the object factor can be found by extracting the RNA (ribonucleic acid) from the cultured cells and detecting by Northern Blotting, RT-PCR and the like. In addition, a cell surface differentiation marker is detected by ELISA and flow cytometry using a specific antibody, and the effect of the object factor on the differentiation and proliferation can be observed.

When cells and/or tissues are cultivated by the culture method of the present invention, culture tools generally used for cell culture such as schale, flask, plastic bag, Teflon (registered trade mark) bag, dish, schale, dish for tissue culture, multidish, microplate, microwell plate, multiplate, multiwell plate, chamber slide, tube, tray, culture bag, roller bottle and the like can be used for cultivation. While the materials of these culture tools are not particularly limited, for example, plastic and the like such as glass, polyvinyl chloride, cellulose-based polymer, polystyrene, polymethylmethacrylate, polycarbonate, polysulfone, polyurethane, polyester, polyamide, polystyrene, polypropylene and the like can be mentioned. Moreover, these plastics may be applied with various surface treatments (e.g., plasma treatment, corona treatment etc.). Furthermore, these culture tools may be coated in advance with an extracellular matrix, a cell adhesion molecule and the like. Examples of the coating material include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin, hyaluronic acid, superfamily, Matrigel, poly-D-lysine, poly-L-lysine, chitin, chitosan, sepharose, alginic acid gel, hydrogel, cleavage fragments thereof and the like. These coating materials having an amino acid sequence artificially altered by gene recombination techniques can also be used. A coating material for inhibiting adhesion of the cells and/or tissues to culture tools can also be used. Examples of the coating material include, but are not limited to, silicon, poly(2-hydroxymethylmethacrylate), poly(2-methacryloyloxyethylphosphoryl choline) and the like.

The cells and/or tissues can also be cultured by automatically conducting cell seeding, medium exchange, cell image obtainment, and recovery of cultured cells, under a mechanical control and under a closed environment while controlling pH, temperature, oxygen concentration and the like and using a bioreactor and an automatic incubator capable of high density culture. As a method for supplying a new medium and feeding the required substances to the cells and/or tissues during the culture using such apparatuses, fed-batch culture, continuous culture and perfusion culture are available, and all these methods can be used for the culture method of the present invention.

When cells and/or tissues are cultured using the particular compound of the present invention, a medium composition can be prepared by mixing a medium used for culturing cells and/or tissues, and the aforementioned polymer compound having an anionic functional group, which shows a reduced amount of contaminating divalent metal cations. The present invention provides a production method of the medium composition.

Examples of the medium include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), StemlineII (manufactured by Sigma Aldrich), QBSF-60 (manufactured by Qualitybiological), StemPro hESC SFM (manufactured by Invitrogen), mTeSR1 or 2 medium (manufactured by STEMCELL Technologies), Sf-900II (manufactured by Invitrogen), Opti-Pro (manufactured by Invitrogen), and the like.

When the cells and/or tissues are derived from a plant, a medium obtained by adding auxins and, where necessary, a plant growth control substance (plant hormone) such as cytokinins and the like at a suitable concentration to a basic medium such as Murashige Skoog (MS) medium, Linsmaier Skoog (LS) medium, White medium, Gamborg's B5 medium, niche medium, hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokinins include, but are not limited to, kinetin, benzyladenine (BA), zeatin and the like. For example, cytokinins can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination. Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various proliferation factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating agent (M-CSF), granulocyte-macrophage colony stimulating agent (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-Mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid gland stimulation hormone, thyrotropin releasing hormone, cortisol, aldosterone, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-α (TGF-α), transforming growth factor-β (TGF-β), macrophage inflammatory protein-1α (MIP-1α), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF) hepatocyte growth factor (HGF), leukemia inhibitory factor (LIF), protease nexin I, protease nexin II, platelet-derived growth factor (PDGF), choline vasoactive differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunity globulin superfamily, Matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include Sulfonamides and preparations, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, Piromidic acid, ciprofloxacin, cinoxacin, norfloxacin, perfloxacin, Rosaxacin, ofloxacin, enoxacin, pipemidic acid, sulbactam, clavulanic acid, β-bromopenisilanic acid, β-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, Chlortetracycline, oxytetracycline, tetracycline, demeclocycline, doxycycline, methacycline, and minocycline.

In a preferable embodiment, the medium contains metal cation, for example, divalent metal cation (calcium ion, magnesium ion, zinc ion, iron ion and copper ion etc.), preferably calcium ion. Calcium ion is contained in 0.1-10 mM, preferably 0.5-3.0 mM. When a metal cation is contained, polymer compounds having an anionic functional group gather via the metal cation; the polymer compounds having an anionic functional group form a tertiary network; or the polymer compounds having an anionic functional group form a microgel via the metal cation, whereby a structure capable of suspension culture of cells or tissues can be formed.

The production method of the present invention is characterized by the use of a polymer compound having an anionic functional group (e.g., deacylated gellan gum) with a reduced amount of contaminating divalent metal cations as a polymer compound having an anionic functional group. Since commercially available polymer compounds having an anionic functional group (e.g., deacylated gellan gum) are generally hardly soluble in water, a heat treatment such as autoclave and the like is sometimes necessary for dissolving them in water. The present inventors investigated the cause of being hardly water-soluble to find divalent metal cation contaminating the polymer compound as the cause, and succeeded in forming a structure capable of suspension culture of cells or tissues when a polymer compound having an anionic functional group is added to a liquid medium, by improving the water-solubility of the polymer compound having an anionic functional group (e.g., deacylated gellan gum) by removing the contaminating divalent metal cation.

Examples of the divalent metal cation include calcium ion, magnesium ion, zinc ion, iron ion, copper ion and the like. Particularly, the amount of contaminating calcium ion is decreased.

In one embodiment, a polymer compound having an anionic functional group, which is substantially free of a divalent metal cation (e.g., deacylated gellan gum), is used. "substantially free of a divalent metal cation" means that the total divalent metal cation in the polymer compound after treatment is not more than 900 ppm, preferably not more than 600 ppm, more preferably not more than 300 ppm, most preferably nil. Particularly, Ca is generally not more than 500 ppm, preferably not more than 300 ppm, more preferably not more than 100 ppm, and Mg is generally not more than 300 ppm, preferably not more than 200 ppm, more preferably not more than 100 ppm. In a further aspect, the amount of contaminating calcium ion is, for example, not more than 750 ppm, preferably not more than 500 ppm, more preferably not more than 300 ppm, further preferably not more than 100 ppm, most preferably not more than 50 ppm, and the amount of contaminating magnesium ion is, for example, not more than 300 ppm, preferably not more than 200 ppm, more preferably not more than 100 ppm, further preferably not more than 50 ppm, most preferably not more than 25 ppm.

As for the amount of contaminating divalent metal cation in a polymer compound having an anionic functional group, which is substantially free of a divalent metal cation, when DAG is used, Ca in treated DAG is generally not more than 500 ppm, preferably not more than 300 ppm, more preferably not more than 100 ppm, and Mg is generally not more than 300 ppm, preferably not more than 200 ppm, more preferably not more than 100 ppm. In a further aspect, the amount of contaminating calcium ion in treated DAG is, for example, not more than 750 ppm, preferably not more than 500 ppm, more preferably not more than 300 ppm, further preferably not more than 100 ppm, most preferably not more than 50 ppm, and the amount of contaminating magnesium ion is, for example, not more than 300 ppm, preferably not more than 200 ppm, more preferably not more than 100 ppm, further preferably not more than 50 ppm, most preferably not more than 25 ppm. Most preferably, treated DAG does not contain divalent metal cation.

In the case of deacylated gellan gum, by reducing the amount of contaminating divalent metal cation in this way, for example, not less than 1500 mg of a deacylated gellan gum powder can be completely dissolved in 100 ml of pure water at 25° C.

Generally, since commercially available polymer compounds having an anionic functional group (e.g., deacylated gellan gum) considerably contain divalent metal cations, the divalent metal cations need to be removed. Therefore, in one embodiment, the production method of the present invention includes a step of subjecting a polymer compound having an anionic functional group to a divalent metal cation removal treatment. By this divalent metal cation removal treatment, a polymer compound having an anionic functional group with a reduced amount of contaminating divalent metal cations (preferably, a polymer compound having an anionic functional group, which is substantially free of a divalent metal cation(s)) can be obtained.

Examples of the method for removing divalent metal cations include, but are not limited to, a cation exchanger treatment, a chelating agent treatment, a precipitation method, a solvent extraction method, an ion exchange membrane method and the like.

In consideration of contamination of a medium composition, a cation exchanger treatment is preferable.

A cation exchanger may be a cation exchanger that exchanges a divalent metal cation with a monovalent metal cation.

As the cation exchanger, a weak acidic cation exchange resin, a strong acidic cation exchange resin, a chelate resin and the like can be mentioned.

While these cation exchange resins are not particularly limited, hydrogen type and sodium type can be used and, in consideration of the operability, sodium type is preferable. When a hydrogen type cation exchange resin is used, an anionic functional group in a polymer compound (e.g., deacylated gellan gum) after the treatment shows a structure of acid rather than salt. Therefore, an aqueous solution of the polymer compound after the treatment becomes acidic, which causes a risk of hydrolysis of the polymer compound by acid. Therefore, a neutralization treatment with an alkali is generally necessary after the treatment with a hydrogen type cation exchange resin. In contrast, when a sodium type cation exchange resin is used, an anionic functional group in a polymer compound after the treatment shows a structure of sodium salt. Therefore, an aqueous solution of the polymer compound after the treatment does not show strong acidity even without a neutralization treatment, and the risk of hydrolysis of the polymer compound by acid can be reduced.

In addition, hydrogen type, or sodium type cation exchange resin may be used after converted to a potassium type or an ammonium type.

While the method of contacting a polymer compound and an ion exchange resin is not particularly limited, it includes a column type method and a batch type method.

In the column type, a cation exchange resin is filled in a column, a solution of the polymer compound is flown, and the eluted solution is recovered. In the batch type, a solution of a cation exchange resin and a polymer compound is stirred or shaken to the degree the resin is suspended, reacted for a given time, and the supernatant or filtrate without the resin is recovered.

A cation exchanger treatment can be performed by mixing a polymer compound having an anionic functional group with a cation exchanger to cause adsorption of divalent metal cations in the polymer compound onto the cation exchanger, and isolating, from the mixture, the above-mentioned polymer compound after removal of the divalent metal cations. A cation exchanger is well known to those of ordinary skill in the art, and conventional one can be used.

For example, in the case of a sodium type cation exchange resin (batch type), the cation exchange resin and a polymer compound are mixed and heated, allowed to cool to room temperature, supernatant or filtrate without the resin is collected and added to lower alcohol (e.g., isopropyl alcohol), and the resulting suspending solid content is squeezed to remove water, and dried (e.g., in vacuum oven), whereby a dry powder of the above-mentioned polymer compound after removal of divalent metal cations can be obtained.

In the case of a sodium type cation exchange resin (column type), a cation exchange resin is filled in a column, a solution of the molecule compound is flown, the eluted solution is collected and added to lower alcohol (e.g., isopropyl alcohol), and the resulting suspending solid content is squeezed to remove water, and dried (e.g., in vacuum oven), whereby a dry powder of the above-mentioned polymer compound after removal of divalent metal cations can be obtained.

In the case of a hydrogen type cation exchange resin (batch type), the cation exchange resin and a polymer compound are mixed and heated, allowed to cool to room temperature, neutralized with alkali (e.g., aqueous solution monovalent hydroxide salt of lithium, sodium, potassium, rubidium, cesium etc.), the solution is added to lower alcohol (e.g., isopropyl alcohol), and the resulting suspending solid content is squeezed to remove water, and dried (e.g., in vacuum oven), whereby a dry powder of the above-mentioned polymer compound after removal of divalent metal cations can be obtained.

Examples of the weak acidic cation exchange resin include, but are not limited to, Amberlite (registered trade mark)(CG-50 TypeI, IRC50, IRC76, IRC86, IRP64), Diaion™ (CWK30/S, WK10, WK20, WK40, WK100, WT01S), DOWEX (registered trade mark)(MAC-3) and the like.

Examples of the strong acidic cation exchange resin include, but are not limited to, Amberlite (registered trade mark)(200, 200C, IR120H, IR122Na, 15, 1200H, IRN77, CG-120, IRP69), Amberjet (registered trade mark)(1200), Amberlyst (registered trade mark)(15 (Dry), 16, 36), Diaion (registered trade mark)(EXC04, HPK25, PK208, PK212, PK216, PK220, PK228 L, RCP160 M, SK1B, SK1BS, SK104, SK110, SK112, SK116, UBK510 L, UBK555), DOWEX (registered trade mark)(50Wx2, 50Wx4, 50Wx8, DR-2030, DR-G8, HCR-W2, MSC, 650C, 6500 UPW, G-26, 88, 88, M-31, 99K/320, 99K/350, Marathon C, N-406), Lewatit (registered trade mark)(MonoPlusS100, MonoPlusSP112) and the like.

Examples of the chelate resin include, but are not limited to, Amberlite (registered trade mark)(IRC-748), Ambersep (registered trade mark)(GT74) Sumichelate (registered trade mark)(MC700, MC760, MC850, MC900, MC960, CR2), Diaion™ (CR11), DOWEX (registered trade mark) (M4195), Duolite (registered trade mark)(0467, GT73, C548, C747), Lewatit (registered trade mark)(TP207, T0208, TP260) and the like.

In a batch type treatment, for example, when DAG is used as the polymer compound, the amount of resin is generally 0.5-10 ml, preferably 1-10 ml, more preferably 1-5 ml, further preferably 2-4 mL, per 1 g of DAG; the DAG treatment concentration is 0.001%-5.0% (w/v), preferably 0.1-2.0% (w/v), more preferably 0.1-1.5% (w/v), further preferably 0.1-1.0% (w/v); the treatment temperature is generally 10-120° C., preferably 25-120° C., more preferably 40-70° C.; and the treatment time is generally 0.5 hr-24 hr, preferably 0.5 hr-2 hr, more preferably 0.5 hr-1 hr.

In a column type treatment using DAG as the polymer, the amount of resin is 1-10 ml, preferably 1-5 ml, more preferably 2-4 mL, per 1 g of DAG; the DAG treatment concentration is 0.001%-5.0%, preferably 0.1-1.0%; the treatment temperature is 5-40° C., preferably 10-30° C.; and the treatment time is 0.5 hr-24 hr, preferably 0.5 hr-1 hr.

In one embodiment, a suspension of a polymer compound having an anionic functional group (e.g., deacylated gellan gum) in water is mixed with a cation exchanger (e.g., cation exchange resin), and the mixture is stirred or shaken to the degree the resin is suspended (batch method). The aforementioned suspension contains an insoluble material of a polymer compound having an anionic functional group. This embodiment is characterized by mixing a polymer compound having an anionic functional group, which is not completely dissolved in water and in a suspending state, with a cation exchanger. The polymer compound having an anionic functional group in the suspension can be hardly soluble in water since it contains contaminating divalent metal cations. A polymer compound having an anionic functional group hardly soluble in water can contain, for example, 2000 ppm (e.g., 2700 ppm) or more of divalent metal cations (e.g., calcium ion). As a cation exchanger, those mentioned above can be used. Preferably, a sodium type cation exchanger (e.g., cation exchange resin) is used. This is because, as mentioned above, an aqueous solution of a polymer compound after treatment does not show strong acidity even without a neutralization treatment, and the risk of hydrolysis by the acid of the polymer compound can be reduced. When treated with a proton type cation exchanger, the polymer compound (e.g., deacylated gellan gum) is easily gelated particularly at low temperature (not more than 30° C.), which sometimes degrades operability since the filter for removal of the exchanger is clogged and the like. Such risk can be avoided by using a sodium type cation exchanger. A polymer compound having an anionic functional group and a cation exchange resin may be mixed under heating conditions so that divalent metal cations can be removed efficiently, though such is not essential. The temperature is generally 10-90° C., preferably 10-70° C., 20-70° C., 30-70° C., 30-60° C., 30-50° C., or 30-40° C. Particularly, the removal efficiency of divalent metal cations is superior at 30-70° C. When an aqueous solution of a polymer compound having an anionic functional group, which is free of an insoluble material of the polymer compound, is treated with a cation exchange resin, a heat treatment is required twice when the polymer compound having an anionic functional group is dissolved in water, and when it is treated with the cation exchange resin. In contrast, in this embodiment, since a suspension of the polymer compound having an anionic functional group is directly treated with a cation exchange resin, a reaction to remove divalent metal cations in the suspension by the cation exchange resin, and dissolution of a polymer compound having an anionic functional group and showing increased water-solubility in water by the removal of the divalent metal cations, proceed simultaneously. As a result, a heat treatment is necessary only once and the treatment time can be shortened and the treatment operation can be simplified. Furthermore, when an aqueous solution of a polymer compound having an anionic functional group and free of insoluble material of the polymer compound is treated with a cation exchange resin, heating at a high temperature (e.g., not less than 90° C.) is sometimes necessary for first dissolving a hardly soluble polymer compound having an anionic functional group in water. In this embodiment, however, such heating is not necessary and the removal of divalent metal cation by a cation exchange resin and dissolution of a polymer compound having an anionic functional group in water proceed simultaneously under milder conditions (e.g., 10-70° C.). Therefore, decomposition of a polymer compound having an anionic functional group due to heating can be avoided. When an aqueous solution of a polymer compound having an anionic functional group and free of insoluble material of the polymer compound is treated with a cation exchange resin, for example, deacylated gellan gum, the deacylated gellan gum concentration in the aqueous solution to be the treatment target can only be increased to about 0.5% (w/v). In this embodiment, the deacylated gellan gum content of the suspension to be the treatment target can be increased to more than 0.5% (w/v), for example, not less than 0.6% (w/v), not less than 0.7% (w/v), not less than 0.8% (w/v). While the upper limit value is not particularly limited as long as the whole polymer compound having an anionic functional group is dissolved in water after the cation exchange resin treatment, it is, for example, not more than 2.5% (w/v), preferably not more than 2.0% (w/v), more preferably not more than 1.5% (w/v), further preferably not more than 1.0% (w/v). Using the method of this embodiment, the volume efficiency of the divalent metal cation removal step can be improved. The time of treatment with a cation exchange resin in this embodiment is not particularly limited, and it is generally 0.5 hr-24 hr, preferably 0.5 hr-2 hr, more preferably 0.5 hr-1 hr. By a treatment by the method in this embodiment, an aqueous solution of a polymer compound having an anionic functional group (e.g., deacylated gellan gum) after removal of divalent metal cations can be obtained. The present invention also provides a method of removing a divalent metal cation(s) (e.g., calcium ion) from such polymer compound having an anionic functional group (e.g., deacylated gellan gum). The method may be a purification method of a polymer compound having an anionic functional group (e.g., deacylated gellan gum), or a production method of a polymer compound having an anionic functional group, which is substantially free of a divalent metal cation(s) (e.g., deacylated gellan gum).

As the above-mentioned purification method of the polymer compound after removal of divalent metal cations, a solution after a cation exchanger treatment is dried and a powder of the above-mentioned polymer compound after removal of divalent metal cations can be obtained. In addition, a powder of the above-mentioned polymer compound after removal of divalent metal cations can be obtained by squeezing the suspending solid content produced by adding the solution to lower alcohol (e.g., isopropyl alcohol) to remove water, and drying same (e.g., in vacuum oven). For example, when DAG is used as a polymer compound, the isopropylalcohol amount is 2- to 10-fold, preferably 3- to 5-fold, relative to the DAG solution, the concentration of DAG treatment is 0.001%-5.0%, preferably 0.1-1.0%, the treatment temperature is 0-40° C., preferably 10-25° C., and the treatment time is 0.5 hr-12 hr, preferably 0.5 hr-1 hr.

As a drying method of the obtained solid content, spray dry, freeze-dry, drying by thin film centrifugation evaporator, stir drying, ventilation drying and the like can be mentioned. A powder after drying may be pulverized for use.

In consideration of the solubility in water after drying, spray dry or freeze-dry is preferable. In consideration of the fact that pulverization is not necessary after drying, spray dry is preferable.

A treatment with a chelating agent can be performed by mixing a polymer compound having an anionic functional group with a chelating agent to cause adsorption of divalent metal cations in the polymer compound onto the chelating agent, thus forming a complex, and isolating the above-mentioned polymer compound after removal of the divalent metal cations from the mixture. The chelating agent is not particularly limited as long as it can form a complex with a divalent metal cation(s), and remove same from a polymer compound having an anionic functional group and, for example, organic aminocarboxylate and the like can be mentioned. For example, ethylenediaminetetraacetic acid (EDTA), ethylenediaminetetraacetic acid disodium (EDTA.2Na), ethylene glycol tetraacetic acid (EGTA), nitrilotriacetic acid (NTA), diethylenetriaminepentaacetic acid (DTPA), L-glutamic acid diacetic acid (GLDA) and the like can be mentioned, with preference given to ethylenediaminetetraacetic acid disodium (EDTA.2Na).

For example, the above-mentioned polymer compound is reacted with a chelating agent in water. The mixture is allowed to cool to room temperature, neutralized with alkali (e.g., aqueous solution of monovalent hydroxide salt of lithium, sodium, potassium, rubidium, cesium etc.), added to lower alcohol (e.g., isopropyl alcohol), and the resulting suspending solid content is squeezed to remove water, and dried (e.g., in vacuum oven). Since a complex of divalent metal cations and chelating agent, and excess chelating agent remain dissolved in water, this series of operation affords a dry powder of the above-mentioned polymer compound with a reduced amount of divalent metal cations.

A medium composition capable of suspension culture of cells or tissues is produced by mixing any form of a polymer compound having an anionic functional group, which shows a reduced amount of contaminating divalent metal cations (preferably, a polymer compound having an anionic functional group, which is substantially free of a divalent metal cation), with a medium. The polymer compound may be in the form of a formulated solid such as powder, tablet, pill, capsule, granule, or a liquid such as a solution obtained by dissolving in an appropriate solvent using a solubilizer or a suspension, or may be bonded to a substrate or a single substance. Examples of the additive used for formulating include preservatives such as p-oxybenzoic acid esters and the like; excipients such as lactose, glucose, sucrose, mannit and the like; lubricants such as magnesium stearate, talc and the like; binders such as polyvinyl alcohol, hydroxypropylcellulose, gelatin and the like; surfactants such as fatty acid ester and the like; plasticizers such as glycerol and the like; and the like. These additives are not limited to those mentioned above, and can be selected freely as long as they are utilizable for those of ordinary skill in the art.

In addition, a polymer compound having an anionic functional group, which shows a reduced amount of contaminating divalent metal cations, may be sterilized as in necessary. The sterilization method is not particularly limited, and, for example, radiation sterilization, ethylene oxide gas sterilization, autoclave sterilization, filter sterilization and the like can be mentioned. When filter sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited, it is preferably 0.1 μm to 10 μm, more preferably 0.1 μm to 1 μm, most preferably 0.1 μm to 0.5 μm. These sterilization treatments can be applied regardless of whether a polymer compound having an anionic functional group, which shows a reduced amount of contaminating divalent metal cations, is in a solid state or in a solution state.

In one embodiment, an aqueous solution of a polymer compound having an anionic functional group, which shows a reduced amount of contaminating divalent metal cations (preferably, a polymer compound having an anionic functional group, which is substantially free of a divalent metal cation(s)) (used as medium additive) is used for the production method of the present invention. The aqueous solution can be obtained by dissolving a solid (e.g., powder) of a polymer compound having an anionic functional group, which shows a reduced amount of contaminating divalent metal cations, in a physiological aqueous solvent. As mentioned above, since a polymer compound having an anionic functional group, which shows a reduced amount of contaminating divalent metal cations, shows high solubility in water, it can be dissolved in an aqueous solvent without requiring a heat treatment. Particularly, in the case of DAG, a high concentration solution containing DAG at a concentration of 1.0-1.5% (weight/volume) in an aqueous solution can be produced (commercially available DAG has a difficult problem of poor operability, since it essentially requires a heat treatment for dissolution and, at a high concentration of not less than 1%, becomes a gel when it is dissolved by a heat treatment and cooled to room temperature).

The temperature for dissolution is, for example, 5-60° C., preferably 5-40° C., more preferably 10-30° C., relative to water.

Examples of the aqueous solvent include, but are not limited to, water, dimethyl sulfoxide (DMSO) and the like. As the aqueous solvent, water is preferable.

The aqueous solvent may contain an appropriate buffering agent or salt. While the aqueous solvent may or may not contain divalent metal cations, divalent metal cations are not contained in a preferable embodiment. When an aqueous solvent is free of divalent metal cations, a polymer compound having an anionic functional group does not easily form a structure capable of suspension culture of cells or tissues in the aqueous solution, and can be stably preserved in a dissolution state in water.

The concentration of a polymer compound having an anionic functional group in an aqueous solution is not particularly limited as long as the polymer compound is stably dissolved. For example, it is 0.0001% to 1.5% (weight/volume), preferably 0.01% to 0.5% (weight/volume), more preferably 0.01% to 0.3% (weight/volume).

It is also possible to further add an additive to enhance the effect of a polymer compound having an anionic functional group, or lower the concentration when in use, to the above-mentioned medium additive. As an example of such additive, one or more kinds of polysaccharides including guargum, tamarind gum, alginic acid propylene glycol ester, locust bean gum, gum arabic, tara gum, tamarind gum, methylcellulose and the like can be mixed.

An aqueous solution of a polymer compound having an anionic functional group may be sterilized (filtration, autoclave sterilization etc.). The aforementioned aqueous solution after sterilization may be mixed with a liquid medium (an aqueous solution of the medium) for use. Alternatively, an aqueous solution of the aforementioned polymer compound and a liquid medium prepared by dissolving a powder medium in water (an aqueous solution of the medium) may be mixed and sterilized for use. Sterilization of the aforementioned aqueous solution and liquid medium may be performed separately before mixing.

As the sterilization method, the aforementioned methods can be mentioned, with preference given to filtration sterilization. The size of the fine pores for filtration sterilization is as mentioned above. Generally, a membrane filter with a pore size of 0.22 μm is used for the filtration sterilization step. Preferable pore size is 0.1 μm.

For example, when DAG is used as a polymer compound, the concentration range of aqueous DAG solution permitting filtration sterilization is 0.0001-2%, practically preferably 0.0001-1%.

In one embodiment, an aqueous solution of a polymer compound having an anionic functional group, which shows a reduced amount of contaminating divalent metal cations (e.g., DAG) (preferably, a polymer compound having an anionic functional group, which is substantially free of a divalent metal cation(s)) is autoclave sterilized, and mixed with an aseptic liquid medium. Using an aqueous solution of a polymer compound having an anionic functional group, which shows a reduced amount of contaminating divalent metal cations (e.g., DAG), the risk of causing a decrease in the function of maintaining cells and/or tissues in a suspended state by mixing with a liquid medium, when autoclave sterilization is performed at a low concentration (e.g., not more than 0.03% (weight/volume), preferably 0.001%-0.03% (weight/volume), more preferably 0.005-0.03% (weight/volume)) can be avoided.

Then, a polymer compound having an anionic functional group, which shows a reduced amount of contaminating divalent metal cations (preferably, a polymer compound having an anionic functional group, which is substantially free of a divalent metal cation(s)) is mixed with a medium used for culturing cells and/or tissues such that the concentration of the polymer compound having an anionic functional group in the medium composition is a concentration at which the cells and/or tissues can be uniformly suspended (preferably suspension stood) without substantially increasing the viscosity of the liquid. Preferably, an aqueous solution of the polymer compound having an anionic functional group is sterilized and mixed with a liquid medium (an aqueous solution of the medium).

The mixing ratio of aqueous solution of a polymer compound having an anionic functional group:liquid medium (an aqueous solution of the medium) is 1:99-99:1, preferably 10:90-90:10, more preferably, 20:80-80:20.

As the order of mixing, an aqueous solution of a polymer compound having an anionic functional group may be added to a liquid medium (an aqueous solution of the medium), or a liquid medium (an aqueous solution of the medium) may be added to an aqueous solution of a polymer compound having an anionic functional group.

The concentration of such polymer compound having an anionic functional group is as mentioned above. For example, a polymer compound having an anionic functional group, which shows a reduced amount of contaminating divalent metal cations (preferably, a polymer compound having an anionic functional group, which is substantially free of a divalent metal cation(s)) is mixed with a medium used for culturing cells and/or tissues such that the concentration of the polymer compound having an anionic functional group in the medium composition is 0.0005% to 1.0% (weight/volume), preferably 0.001% to 0.4% (weight/volume), more preferably 0.005% to 0.1% (weight/volume), further preferably 0.005% to 0.05% (weight/volume).

For example, in the case of deacylated gellan gum, it is added to a medium at 0.001% to 1.0% (weight/volume), preferably 0.003% to 0.5% (weight/volume), more preferably 0.005% to 0.1% (weight/volume), more preferably 0.01% to 0.05% (weight/volume), most preferably, 0.01% to 0.02% (weight/volume). In the case of xanthan gum, it is added to a medium at 0.001% to 5.0% (weight/volume), preferably 0.01% to 1.0% (weight/volume), more preferably 0.05% to 0.5% (weight/volume), most preferably, 0.1% to 0.2% (weight/volume). In the case of κ-carageenan and locust bean gum, they are added to a medium at 0.001% to 5.0% (weight/volume), preferably 0.005% to 1.0% (weight/volume), more preferably 0.01% to 0.1%, most preferably, 0.03% to 0.05% (weight/volume).

The concentration can be calculated by the following formula.

Concentration (%)=weight (g) of particular compound/volume (ml) of medium composition× 100

By mixing a polymer compound having an anionic functional group, which shows a reduced amount of contaminating divalent metal cations (preferably, a polymer compound having an anionic functional group, which is substantially free of a divalent metal cation(s)) with a medium, a structure capable of suspension culture of cells or tissues in the medium is formed, and the medium composition of the present invention can be obtained. Since a medium generally contains metal cations at a concentration sufficient for: polymer compounds having an anionic functional group gathering via the metal cations; the polymer compounds having an anionic functional group forming a tertiary network; or polymer compounds having an anionic functional group forming a microgel via the metal cations, the medium composition of the present invention can be obtained by simply adding a polymer compound having an anionic functional group, which shows a reduced amount of contaminating divalent metal cations, to the medium.

Examples of the production method of the medium composition of the present invention are shown below, which are not to be construed as limitative. A polymer compound having an anionic functional group, which shows a reduced amount of contaminating divalent metal cations (preferably, a polymer compound having an anionic functional group, which is substantially free of a divalent metal cation(s)), is added to ion exchange water or ultrapure water. Then, the mixture is stirred at a temperature at which the particular compound can be dissolved (e.g., 5-60° C., preferably 5-40° C., more preferably 10-30° C.) to allow for dissolution to a transparent state.

After dissolving, the mixture is sterilized (e.g., autoclave sterilization at 121° C. for 20 min, filter filtration). The aforementioned sterilized aqueous solution is added with stirring (e.g., homomixer etc.) to a given medium to be used for static culture to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer. Furthermore, the medium composition of the present invention can be filtrated through a filter after mixing. The size of the pore of the filter to be used for the filtration treatment is 5 μm to 100 μm, preferably 5 μm to 70 μm, more preferably 10 μm to 70 μm.

For example, when deacylated gellan gum is prepared, deacylated gellan gum with a reduced amount of contaminating divalent metal cations (preferably, deacylated gellan gum substantially free of a divalent metal cation(s)) is added to ion exchange water or ultrapure water at 0.0001% to 1.5% (weight/volume), preferably 0.01% to 0.5% (weight/volume), more preferably 0.01% to 0.3% (weight/volume). Then, the aforementioned deacylated gellan gum is dissolved to a transparent state by stirring with heating at any temperature as long as dissolution is possible, which may be 5 to 60° C., preferably 5 to 40° C., more preferably 10 to 30° C. After dissolution, the mixture is sterilized with autoclave at, for example, 121° C. for 20 min or filter filtration. For example, the aqueous solution is added to a liquid medium such as DMEM/F-12 medium with stirring by a homomixer and the like to a desired final concentration (for example, when the final concentration is 0.015%, the ratio of 0.3% aqueous solution:medium is 1:20), and the mixture is homogeneously mixed. Alternatively, a liquid medium such as DMEM/F12 medium and the like is added by pipette to the aqueous solution to a desired final concentration (e.g., when the final concentration is 0.015%, the ratio of 0.3% aqueous solution:medium is 1:20), and uniformly mixed by pipetting. The mixing method of the aqueous solution and the medium is not particularly limited, and may be manual mixing such as pipetting etc., or mixing with an instrument such as magnetic stirrer, mechanical stirrer, homomixer and homogenizer. Furthermore, the medium composition of the present invention can be filtrated through a filter after mixing. The size of the pore of the filter to be used for the filtration treatment is 5 μm to 100 μm, preferably 5 μm to 70 μm, more preferably 10 μm to 70 μm.

Those of ordinary skill in the art can freely select the form and state of the cells and/or tissues to be cultured by the method of the present invention. Preferable specific examples thereof include, but are not particularly limited to, a state in which the cells and/or tissues are singly dispersed in the medium composition, a state in which the cells and/or tissues are attached to the surface of a carrier, a state in which the cells and/or tissues are embedded inside a carrier, a state in which plural cells assemble and form cell aggregations (spheres), or a state in which two or more kinds of cells assemble and form cell aggregations (spheres), and the like. More preferred are a state in which the cells and/or tissues are attached to the surface of a carrier, a state in which the cells and/or tissues are embedded inside a carrier, a state in which plural cells assemble and form cell aggregations (spheres), and a state in which two or more kinds of cells assemble and form cell aggregations (spheres). Further preferred are a state in which the cells and/or tissues are attached to the surface of a carrier, a state in which plural cells assemble and form cell aggregations (spheres), and a state in which two or more kinds of cells assemble and form cell aggregations (spheres). Among these states, the state with forming cell aggregations (spheres) can be mentioned as the most preferable state to be cultured by the culture method of the present invention, since cell-cell interactions and cell structures close to those in the in vivo environment are reconstructed, long-term culture can be performed while maintaining the cell function, and also cell recovery is relatively easy.

As a carrier to support the cells and/or tissues on the surface, microcarrier and glass bead composed of various polymers, ceramic bead and the like can be mentioned. As examples of the polymers, vinyl resin, urethane resin, epoxy resin, polystyrene, polymethylmethacrylate polyester, polyamide, polyimide, silicon resin, phenol resin, melamine resin, urea resin, aniline resin, ionomer resin, polycarbonate, collagen, dextran, gelatin, cellulose, alginates, mixtures thereof, and the like can be used. The carrier may be coated with a compound that enhances cell adhesion or release of substance from the cells. As examples of such coating materials, poly(monostearoylglyceride co-succinic acid), poly-D,L-lactid-co-glycolide, sodium hyaluronate, n-isopropylacrylamide, collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, further, cleavage fragments thereof, and the like can be mentioned. Here, two or more kinds of the coating materials may be combined. Furthermore, one or more kinds of polysaccharides such as guargum, tamarind gum, locust bean gum, gum arabic, tara gum, tamarind gum, methylcellulose and the like can also be mixed with a medium to be used for culture of a carrier supporting the cells and/or tissues on the surface. The carrier may also contain a magnetic material, for example, ferrite. The diameter of the carrier is several tens of micrometers to several hundreds of micrometers, more preferably 100 μm to 200 μm, and its specific gravity is preferably close to 1, more preferably 0.9-1.2, particularly preferably about 1.0. Examples of the carrier include, but are not limited to, Cytodex 1 (registered trade mark), Cytodex 3 (registered trade mark), Cytoline 1 (registered trade mark), Cytoline 2 (registered trade mark), Cytopore 1 (registered trade mark), Cytopore 2 (registered trade mark), (above, GE Healthcare Life Sciences), Biosilon (registered trade mark) (NUNC), Cultispher-G (registered trade mark), Cultispher-S (registered trade mark) (above, Thermo SCIENTIFIC), HILLEXCT (registered trade mark), ProNectinF-COATED (registered trade mark), and HILLEXII (registered trade mark) (Solo Hill Engineering) and the like. The carrier may be sterilized as necessary. The sterilization method is not particularly limited and, for example, radiation sterilization, ethylene oxide gas sterilization, autoclave sterilization, dry heat sterilization, and the like can be mentioned. The method for culturing animal cells using the carrier is not particularly limited, and a culture method using a general flow layer-type culture vessel or filling layer-type culture vessel, and the like can be used. Here, a carrier supporting cells and/or tissues on the surface and using a medium composition comprising the structure of the particular compound of the present invention allows for uniform dispersion even without an operation of shaking and the like. As a result, the object cells and/or tissues can be cultured without losing cell function. The cells and/or tissues cultured by this method can be collected by performing centrifugation and filtration treatment while the cells and/or tissues are supported by the carrier after the culture. In this case, centrifugation and filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. Furthermore, cultured carriers can be recovered with a magnetic force by encapsulating a material having magnetism, such as ferrite, in the carrier. The cells and/or tissues cultured by this method can be collected by releasing the carrier by using various chelating agents, a heat treatment, or an enzyme.

When cells and/or tissues are embedded inside a carrier, materials composed of various polymers can be selected as the carrier. As examples of such polymers, collagen, gelatin, alginates, chitosan, agarose, poly glycolic acid, polylactic acid, fibrin adhesive, polylactic acid-polyglycolic acid copolymer, proteoglycan, glycosaminoglycan, sponge such as polyurethane foam, DseA-3D (registered trade mark), poly N-substituted acrylamide derivative, poly N-substituted methacrylamide derivative, and copolymers thereof, polyvinyl methylether, polypropylene oxide, polyethylene oxide, temperature sensitive polymers such as partially acetified polyvinyl alcohol, polyacrylamide, polyvinyl alcohol, methylcellulose, nitrocellulose, cellulose butyrate, polyethylene oxide, and hydrogels such as poly(2-hydroxyethylmethacrylate)/polycaprolactone and the like can be mentioned. In addition, it is possible to prepare a carrier for embedding cells by using two or more kinds of these polymers. Furthermore, the carrier may have a physiologically active substance besides these polymers. As examples of the physiologically active substance, cell growth factors, differentiation inducing factors, cell adhesion factors, antibodies, enzymes, cytokines, hormones, lectins, extracellular matrices and the like can be mentioned, and a plurality of these can also be contained. Furthermore, one or more kinds of thickeners such as guargum, tamarind gum, alginic acid propyleneglycol ester, locust bean gum, gum arabic, tara gum, tamarind gum, methylcellulose and the like can also be mixed with a medium used for culture of a carrier embedding cells and/or tissues.

The method for embedding the cells and/or tissues in these carriers is not particularly limited and, for example, a method including aspirating a mixture of the cells and the aforementioned polymers with a syringe and dropwise adding them to a medium from around 25 G-19 G injection needle, or dropwise adding to a medium using a micropipette, and the like can be used. The size of the bead-like carrier formed here is determined by the shape of the tip of a tool used for the dropwise addition of a mixture of the cell and the aforementioned polymers, which is preferably several tens of micrometers to several thousands of micrometers, more preferably 100 μm to 2000 μm. The number of cells that can be cultured on a bead-like carrier is not particularly limited, and can be freely selected according to the bead size. For example, 5 million cells can be embedded in a bead-like carrier with a diameter of about 2000 μm. Within the carrier, the cells may be singly dispersed or plural cells may assemble to form a cell aggregate. Here, using a medium composition comprising the structure of the particular compound of the present invention allows a carrier having the cells and/or tissues embedded therein to uniformly disperse even without an operation of stirring and the like. As a result, the object cells and/or tissues can be cultured without losing cell function. The cells and/or tissues cultured by this method can be collected by performing centrifugation and filtration treatment while the cells and/or tissues are embedded in the carrier after the culture. In this case, centrifugation and filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. The cells and/or tissues cultured by this method can be collected by dispersing them by decomposing the carrier by a treatment using various chelating agents, heat, an enzyme and the like.

A method for forming a cell aggregate (sphere) is not particularly limited, and can be appropriately selected by those of ordinary skill in the art. Examples thereof include a method using a container having a cell non-adhesive surface, hanging drop method, gyratory culture method, three-dimensional scaffold method, centrifugation method, a method using coagulation by an electric field or magnetic field and the like. For example, using a method using a container having a cell non-adhesive surface, the object cells are cultured in a culture container applied with a surface treatment to inhibit cell adhesion, whereby a sphere can be formed. When such cell non-adhesive culture container is used, the object cells are first collected, a cell suspension thereof is prepared and plated in the culture container to perform culture. When culture is continued for about 1 week, the cells spontaneously form a sphere. As a cell non-adhesive surface used here, a surface of a culture container generally used such as scahle and the like, which is coated with a substance inhibiting cell adhesion and the like can be used. Examples of such substance include agarose, agar, copolymer of poly-HEMA (poly-(2-hydroxlethylmethacrylate)2-methacryloyloxyethylphosphoryl choline and other monomer (for example, butylmethacrylate etc.) and the like. When cytotoxicity is absent, the substance is not limited thereto.

As a method for forming a cell aggregate (sphere), the methods described in NATURE BIOTECHNOLOGY, VOL. 28, NO. 4, APRIL 2010, 361-366, NATURE PROTOCOLS, VOL. 6, NO. 5, 2011, 689-700, NATURE PROTOCOLS, VOL. 6, NO. 5, 2011, 572-579, Stem Cell Research, 7, 2011, 97-111, Stem Cell Rev and Rep, 6, 2010, 248-259 and the like can also be used.

In addition, a medium used for culture for forming a sphere can also contain a component that promotes formation of a sphere or promotes maintenance thereof. Examples of the component having such effect include dimethyl sulfoxide, superoxide dismutase, caeruloplasmin, catalase, peroxidase, L-ascorbic acid, L-ascorbic acid phosphate ester, tocopherol, flavonoid, uric acid, bilirubin, selenium-containing compound, transferrin, unsaturated fatty acid, albumin, theophylline, forskolin, glucagon, dibutyryl cAMP and the like. As the selenium-containing compound, ROCK inhibitors such as sodium selenite, sodium selenate, dimethyl selenide, hydrogen selenide, Selenomethionine, Se-Methylselenocysteine, Selenocystathionine, Selenocysteine, Selenohomocysteine, adenosine-5'-triphosphoric acid, Se-Adenosylselenomethionine, Y27632, Fasudil (HA1077), H-1152, Wf-536 and the like can be mentioned. To obtain the object cell aggregate having a uniform size, plural concaves having the same diameter as the object cell aggregate can also be introduced onto a cell non-adhesive culture container to be used. When these concaves are in contact with each other or within the range of the diameter of the object cell aggregate, and cells are plated, the plated cells do not form a cell aggregate between concaves but certainly form a cell aggregate with a size corresponding to the volume thereof in the concave, thus affording a cell aggregate population having a uniform size. As the shape of the concave in this case is preferably a hemisphere or cone.

Alternatively, a sphere can also be formed based on a support showing cell adhesiveness. Examples of such support include collagen, polyrotaxane, polylactic acid (PLA), polylactic acid glycolic acid (PLGA) copolymer, hydrogel and the like.

In addition, a sphere can also be formed by co-cultivating with a feeder cell. As a feeder cell to promote sphere formation, any adhesive cell can be used. Preferably, a feeder cell for each kind of cell is desirable. Although not limited, for example, when a sphere of cells derived from the liver or cartilage is formed, examples of the feeder cell include COS-1 cell and vascular endothelial cell as preferable cell types.

Furthermore, a sphere can also be formed using the culture composition containing the structure of the particular compound of the present invention. In this case, the concentration of the particular compound is 0.0005% to 1.0% (weight/volume), preferably 0.001% to 0.3% (weight/volume), more preferably 0.005% to 0.1% (weight/volume), further preferably 0.01% to 0.05% (weight/volume). The sphere is prepared by uniformly dispersing the object cells in a medium containing the structure of the particular compound, and allowing them to cultivate by standing still for 3 days to 10 days. The prepared sphere can be recovered by centrifugation and filtration treatment. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like.

The size of the sphere varies depending on the cell type and culture period and is not particularly limited. When it has a spherical shape or ellipse spherical shape, the diameter thereof is 20 μm to 1000 μm, preferably 40 μm to 500 μm, more preferably 50 μm to 300 μm.

Such sphere can maintain proliferative capacity for not less than 10 days, preferably not less than 13 days, more preferably not less than 30 days, by continuing the standing culture. By regularly further performing, during the standing culture, mechanical division, or a single cell-forming treatment and coagulation, the proliferative capacity can be maintained substantially infinitely.

The culture container to be used for culturing sphere is not particularly limited as long as it generally permits animal cell culture. For example, flask, dish, schale, tissue culture dish, multidish, microplate, microwell plate, multiplate, multiwell plate, chamber slide, schale, tube, tray, culture bag, roller bottle and the like can be mentioned.

The medium to be used for standing culture of sphere can contain a cell adhesion factor, examples thereof include Matrigel, collagen gel, gelatin, poly-L-lysine, poly-D-lysine, laminin and fibronectin. Two or more kinds of these cell adhesion factors can also be added in combination. Furthermore, the medium to be used for culturing sphere can be mixed with a thickener such as guargum, tamarind gum, alginic acid propyleneglycol ester, locust bean gum, gum arabic, tara gum, tamarind gum, methylcellulose and the like.

Using a medium composition comprising the structure of the particular compound of the present invention, uniform dispersion in a medium can be afforded even without an operation of shaking and the like. As a result, the object cells and/or tissues can be cultured as a sphere without losing cell function. The sphere standing cultured by this method can be collected by performing centrifugation or filtration treatment after the culture. In this case, centrifugation or filtration treatment may be performed after adding the liquid medium used. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. The recovered sphere can be dispersed as a single cell by further decomposing by a treatment with various chelating agents, heat, filter, enzyme and the like.

As a method for standing culture of plant-derived cells and/or tissues, callus, which is an undifferentiated plant cell aggregate, can be cultivated. Callus can be induced by a method known for each plant species to be used. For example, a surface of a part of a tissue of a differentiated plant body (e.g., root, stalk, leaf section, seed, growing point, embryo, pollen etc.) is sterilized, where necessary, with 70% alcohol, 1% sodium hypochlorite solution and the like, a tissue section with a suitable size (e.g., about 1-about 5 mm square root section) is cut out with a knife and the like, the tissue section is plated on a callus induction medium sterilized in advance by an aseptic operation using a clean bench and the like, and aseptically cultivated under suitable conditions. The callus induced here may be subjected to liquid culture for mass proliferation, or may also be maintained as a seed strain by passaging in a passage medium. The passage culture may be performed using any of liquid medium and solid medium.

The amount of the plant cell aggregate inoculated when starting the standing culture using the medium composition of the present invention varies depending on the proliferation rate of the object cell, culture manner (batch culture, fed-batch culture, continuous culture etc.), culture period and the like. For example, when a plant cell aggregate such as callus and the like is to be cultivated, it is inoculated to the medium composition of the present invention such that the wet weight of the cell aggregate relative to the medium composition of the present invention is 4-8 (weight/volume (w/v)) %, preferably 5-7 (w/v) %. The particle size of the plant cell aggregate during culture is 3 mm to 40 mm, preferably 3 mm to 20 mm, more preferably 5 mm to 15 mm. As used herein, the "particle size" means a diameter when, for example, the plant cell aggregate has a spherical shape, a major axis when it has an ellipse spherical shape, and the maximum length possible when it has other shape.

The temperature when cells and/or tissues are cultivated is generally 25 to 39° C., preferably 33 to 39° C., for animal cells. The $CO_2$ concentration is generally 4 to 10% by volume in the culture atmosphere, and 4 to 6% volume is preferable. The culture period is generally 3 to 35 days, which may be freely set according to the object of the culture. The culture temperature for plant cells is generally 20 to 30° C. and, when light is necessary, they can be cultured under illuminance conditions of illuminance 2000-8000 lux. While the culture period is generally 3 to 70 days, which may be freely set according to the object of the culture.

When cells and/or tissues are cultivated by the method of the present invention, cells and/or tissues prepared separately are added to the culture composition of the present invention and mixed to give a uniform dispersion. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotation number and frequency can be appropriately set according to the object of those of ordinary skill in the art. When the medium composition needs to be exchanged during the standing culture period, the cells and/or tissues and the medium composition are separated by centrifugation or filtration treatment, and a new medium composition can be added of the cells and/or tissues. Alternatively, the cells and/or tissues are appropriately concentrated by centrifugation or filtration treatment, and a new medium composition can be added to the concentrated liquid. For example, unlimitatively, the gravitational acceleration (G) of centrifugation is 100 G to 400 G, and the size of the pore of the filter used for the filtration treatment is 10 μm to 100 μm. In addition, using magnetic fine particles coated, on the surface, with an antibody that specifically binds to the object cell, the cultured cells and/or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. Exchange of the medium composition can also be performed by using a bioreactor and an automatic incubator capable of conducting under a mechanical control and under a closed environment.

In addition, the present invention provides a purification method of a polymer compound having an anionic functional group.

To be specific, it is a purification method of a polymer compound having an anionic functional group, wherein a suspension of the polymer compound having an anionic functional group in water is treated with a cation exchanger that exchanges a divalent metal cation with a monovalent metal cation to give a polymer compound having an anionic functional group, which shows a reduced amount of contaminating divalent metal cations.

A preferable embodiment of the purification method of the present invention is the same as the aforementioned method of removing divalent metal cations.

The present invention is explained in more detail in the following by specifically describing an Example of the medium composition of the present invention, which is not to be construed as limitative.

EXAMPLES

Reference Example 1 Viscosity Measurement of Medium Containing Deacylated Gellan Gum Heat-Treated at High Temperature and Cell Suspension Test Preparation and Viscosity Measurement of Deacylated Gellan Gum-Containing Medium Deacylated gellan gum (KELCOGEL CG-LA, manufactured by SANSHO Co., Ltd.) was suspended in pure water to 0.4% (w/v), and dissolved by stirring with heating at 90° C. This aqueous solution was allowed to cool to room temperature with stirring, and sterilized at 121° C. for 20 min in an autoclave. A 2-fold concentration of DMEM/F-12 medium (manufactured by Aldrich, 50 mL) and sterilization water (47.5 mL) were placed in a 300 mL tall beaker with stirring by a homomixer (3000 rpm) at room temperature, aqueous deacylated gellan gum solution (2.5 mL) was added, and the mixture was continuously stirred for 1 min to prepare a deacylated gellan gum medium composition with a final concentration of 0.01%. Medium compositions added with aqueous deacylated gellan gum solution with final concentrations of 0.02, 0.03 and 0.05% (w/v) were similarly prepared. The viscosity of the medium compositions was measured using an E type viscometer (manufactured by Toki Sangyo Co., Ltd., Viscometer TVE-22L, standard roter 1° 34'×R24) under 37° C. condition at 100 rpm for 5 min.

Cell Suspension Test of Deacylated Gellan Gum-Containing Medium

Human cervical cancer cell line HeLa (manufactured by DS PHARMA BIOMEDICAL CO., LTD.) was suspended in EMEM medium containing 10% (v/v) fetal bovine serum (manufactured by WAKO) at 250000 cells/mL, the suspension (10 mL) was plated on EZ SPHERE (manufactured by ASAHI GLASS CO., LTD.), and cultured in a $CO_2$ incubator (5% $CO_2$) for 3 days. The obtained suspension (10 mL) of spheres (diameter 100-200 μm) was centrifuged (200 G, 5 min) to allow for sphere sedimentation, and the supernatant was removed to give a sphere suspension (1.0 mL). Successively, the deacylated gellan gum-containing medium prepared above was placed in a 1.5 mL Eppendorf tube by 1.0 mL, and a HeLa cell sphere suspension (10 μL) was further added. The cell aggregate was dispersed by tapping, incubated at 37° C., and the dispersion state of the cells 1 hr later was visually observed.

TABLE 1

| deacylated gellan gum concentration % (w/v) | state | viscosity (mPa · s) | HeLa cell suspension/ sedimentation |
| --- | --- | --- | --- |
| 0.01 | liquid | 1.31 | suspension |
| 0.02 | liquid | 1.92 | suspension |
| 0.03 | liquid | 2.38 | suspension |
| 0.05 | liquid | 3.34 | suspension |

Reference Comparative Example Preparation of Methylcellulose and Collagen-Containing Medium Preparation of Methylcellulose-Containing Medium DMEM/F-12 medium (manufactured by Aldrich, 100 mL) was placed in a 200 mL recovery flask, and methylcellulose (M0387, manufactured by Aldrich, 0.1 g) was added. The mixture was stirred while cooling in an ice bath to dissolve methylcellulose. Using this solution, medium compositions added with the aqueous methylcellulose solution at a final concentration of 0.1, 0.3, 0.6 or 1.0% (w/v) were prepared.

Preparation of Collagen-Containing Medium

A 10-fold concentration of DMEM/F-12 medium (manufactured by Aldrich, 1 mL), a buffer for reconstitution (manufactured by Nitta Gelatin Inc., 1 mL) and pure water (1.5 mL) were added to 0.3% cell matrix type I-A (manufactured by Nitta Gelatin Inc., 6.5 mL), and the mixture was stirred in an ice to give a 0.2% collagen-containing medium. Similarly, medium compositions added with collagen at a final concentration of 0.01, 0.05, 0.1 or 0.2% (w/v) were prepared.

The medium compositions prepared above were subjected to a suspension test of HeLa cell spheres and a viscosity measurement, in the same manner as with the deacylated gellan gum-containing medium. The viscosity of 1.0% (w/v) methylcellulose was measured at 50 rpm due to the measurement range of the apparatus.

TABLE 2

| methylcellulose concentration % (w/v) | state | viscosity (mPa · s) | HeLa cell suspension/ sedimentation |
| --- | --- | --- | --- |
| 0.1 | liquid | 2.31 | sedimentation |
| 0.3 | liquid | 8.15 | sedimentation |
| 0.6 | liquid | 13.0 | sedimentation |
| 1.0 | liquid | 48.2 | sedimentation |

TABLE 3

| collagen concentration % (w/v) | state | viscosity (mPa · s) | HeLa cell suspension/ sedimentation |
| --- | --- | --- | --- |
| 0.01 | liquid | 1.18 | sedimentation |
| 0.05 | liquid/solid (gel) | unmeasurable | suspension |
| 0.1 | solid (gel) | unmeasurable | suspension |
| 0.2 | solid (gel) | unmeasurable | suspension |

Reference Experimental Example

In the following Reference Experimental Examples, the $CO_2$ concentration (%) in a $CO_2$ incubator was shown by % volume of $CO_2$ in the atmosphere. PBS means phosphate buffered saline (manufactured by Sigma Aldrich Japan), and FBS means fetal bovine serum (manufactured by Biological Industries). In addition, (w/v) shows weight per volume.

Reference Experimental Example 1: Cell Proliferation Test by Dispersing Single Cell Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to IMDM medium (manufactured by Gibco) containing 10% (v/v) fetal bovine serum and 10 ng/mL thrombopoietin (manufactured by WAKO). Successively, human leukemia cell line UT7/TPO was plated on a medium composition added with the above-mentioned deacylated gellan gum to 20000 cells/mL, and dispensed to a 6-well flat bottom microplate (manufactured by Corning Incorporated) at 5 mL/well. Similarly, human cervical cancer cell line HeLa (manufactured by DS PHARMA BIOMEDICAL CO., LTD.) was plated at 20000 cell/mL on a medium composition obtained by adding 0.015% (w/v) deacylated gellan gum (KELCOGEL CG-LA, manufactured by SANSHO Co., Ltd.) to EMEM medium containing 10% (v/v) fetal bovine serum (manufactured by WAKO), and the composition was dispensed to a 6-well flat bottom microplate (manufactured by Corning Incorporated) at 5 mL/well. The cell suspensions were cultured while being stood still in a $CO_2$ incubator (5% $CO_2$) for 3 days. Thereafter, a part of the culture medium was recovered, the same amount of Trypan Blue staining solution (manufactured by Invitrogen Corporation) was added, and the number of viable cells was measured by blood cell meter (manufactured by ERMA INC.)

As a result, it was confirmed that, using the above-mentioned medium composition, UT7/TPO cells and HeLa cells can be uniformly cultivated in a suspended state, and efficiently proliferate in the medium composition. The cell numbers of UT7/TPO cells and HeLa cells after static suspension culture for 3 days are shown in Table 4.

TABLE 4

|  | UT7/TPO cells | HeLa cells |
| --- | --- | --- |
| cell number (×10000/mL) | 38 | 40 |

Reference Experimental Example 2: Cell Proliferation Test by Culturing Cell Line-Derived Sphere Human liver cancer cell line HepG2 (manufactured by DS PHARMA BIOMEDICAL CO., LTD.) was suspended in DMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). Similarly, human cervical cancer cell line HeLa (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). The suspension (2.5 mL) of the sphere (diameter 100-200 μm) of each cell line obtained here was centrifuged (200 G, 5 min) to allow for sphere sedimentation, and the supernatant was removed. Successively, the above-mentioned medium (10 mL) was added to the spheres (about 800 spheres) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to DMEM medium containing 10% (v/v) fetal bovine serum.

After static culture of the above-mentioned sphere suspension in a $CO_2$ incubator (5% $CO_2$) at 37° C. for 3 days, a two-fold volume of the medium was added. The mixture was centrifuged (200 G, 5 min) to allow for sphere sedimentation, and the supernatant was removed. At this point, a part of the sphere was taken, and the shape thereof was observed with an optical microscope (manufactured by OLYMPUS, CK30-F100). Successively, the recovered sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (200 G, 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.).

As a result, it was confirmed that, using the above-mentioned medium composition, the spheres of HepG2 cells and HeLa cells could be cultivated in a suspended state, and the cells efficiently proliferate in the medium composition. Furthermore, the medium composition was confirmed to show a small rate of the dead cells as compared to the existing media when the cells were proliferated, and have a superior cell proliferation promoting effect. The sphere cultured in an existing medium sedimented on the bottom of the culture container. Furthermore, the shape of the cultured sphere was observed by an optical microscope. As a result, the medium composition did not show association of the spheres, whereas association of the spheres was observed in the existing media.

Figure 2:
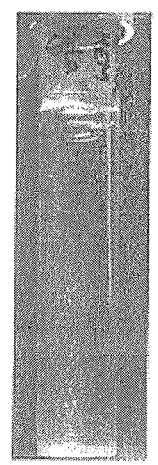
FIG. 2 is a Figure showing that, when spheres of HeLa cells were cultured in the medium composition, the spheres were uniformly dispersed and could be cultured in a suspended state.
Figure 3:
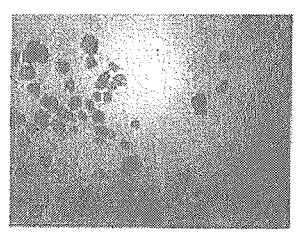
FIG. 3 is a Figure showing that, when spheres of HeLa cells were cultured in the medium composition and observed with a microscope, association of the spheres could be suppressed compared to existing media.
Figure 3:
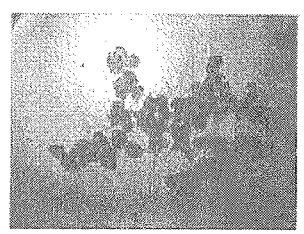

The relative number of the HepG2 cells and HeLa cells is shown in Table 5, wherein the number of the cells cultured in a medium free of deacylated gellan gum is 1. In addition, the relative rate of the dead cells is shown in Table 6, wherein the rate of the dead cells cultured in a medium free of deacylated gellan gum (dead cell number/viable cell number) is 1. The suspended state of the spheres of HepG2 cells and HeLa cells cultured in the medium composition is shown in FIG. 1 and FIG. 2, respectively. Furthermore, the shape of the sphere of the cultured HeLa cells is shown in FIG. 3.

TABLE 5

| deacylated gellan gum | | HepG2 cells | HeLa cells |
|---|---|---|---|
| absent | relative cell number | 1.0 | 1.0 |
| present | relative cell number | 1.7 | 1.5 |

TABLE 6

| deacylated gellan gum | | HepG2 cells | HeLa cells |
|---|---|---|---|
| absent | relative mortality rate | 1.0 | 1.0 |
| present | relative mortality rate | 0.5 | 0.5 |

Reference Experimental Example 3: Cell Proliferation Test by Culturing Cell Line Attached onto Microcarrier Microcarrier Cytodex (registered trade mark) 1 (manufactured by GE Healthcare Life Sciences) was suspended in PBS at 0.02 g/mL, and the suspension was stood overnight. The supernatant was discarded, and the microcarrier was washed twice with fresh PBS. Thereafter, it was suspended again in PBS at 0.02 g/mL, and sterilized at 121° C. for 20 min in an autoclave. Successively, this microcarrier was washed twice with 70% ethanol and three times with PBS, and suspended in DMEM medium containing 10% (v/v) fetal bovine serum (manufactured by WAKO) at 0.02 g/mL. Using this microcarrier suspension, DMEM medium (containing 10% (v/v) fetal bovine serum, 20 mL) containing 120 mg of Cytodex (registered trade mark) 1 and 4000000 HepG2 cells was prepared, and the cell suspension was cultured in a beaker treated in advance with a silicon coating agent (manufactured by AGC TECHNO GLASS Co., Ltd.), with stirring (100 rpm) with a stirrer at 37° C. for 6 hr. At this point, adhesion of HepG2 cells to the microcarrier was confirmed with a microscope. Successively, the microcarrier with the cells adhered thereto was washed twice with DMEM medium containing 10% (v/v) fetal bovine serum, and suspended in the same medium (3 mL).

Figure 4:
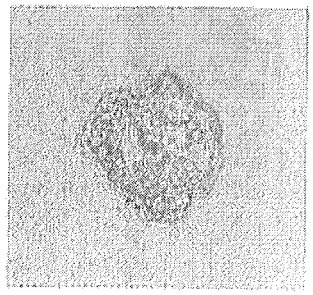
FIG. 4 is a Figure showing that, when microcarriers attached with HepG2 cells was cultured in the medium composition, the HepG2 cells could be proliferated on the microcarrier.

The above-mentioned microcarrier suspension (300 μL) was added to each of DMEM medium (20 mL) containing 10% (v/v) fetal bovine serum and a medium composition obtained by adding, to this medium, 0.015% (w/v) deacylated gellan gum (KELCOGEL CG-LA, manufactured by SANSHO Co., Ltd.), and the mixtures were cultured at 37° C. for 3 days. In the case of the culture medium free of deacylated gellan gum, the mixtures were cultured while stirring (100 rpm) with a stirrer. After culture, the attachment state of the cells on the microcarrier was confirmed with a microscope, and the microcarrier was sedimented by centrifugation (200 G, 5 min). This microcarrier was washed with PBS (10 mL), 1 mL trypsin-EDTA (ethylenediaminetetraacetic acid) solution (manufactured by WAKO) was added, and the mixture was incubated at 37° C. for 5 min. Furthermore, DMEM medium (9 mL) containing 10% (v/v) fetal bovine serum was added, and the microcarrier was removed by Cell Strainer (manufactured by BD Falcon, mesh size 70 μm). The cells were recovered from the obtained filtrate by centrifugation (200 G, 5 min). The cells were suspended in a medium (500 μL), to a part thereof was added the same amount of Trypan Blue staining solution (manufactured by Invitrogen Corporation), and the number of viable cells was measured by a hemocytometer (manufactured by ERMA INC.). As a result, the culture medium free of deacylated gellan gum contained 123,000 cells, but the culture medium containing deacylated gellan gum contained 1,320,000 cells. As mentioned above, it was confirmed that the medium composition containing the structure of the particular compound is superior in the cell proliferation promoting effect as compared to the existing media, even when the cells were cultured using a microcarrier. The attachment state of HepG2 cells after 3 days of microcarrier culture using the medium composition containing the structure of the particular compound is shown in FIG. 4.

Reference Experimental Example 4: Cell Suspension Test Using Cell Line-Derived Sphere Xanthan gum (KELTROL CG, manufactured by SANSHO Co., Ltd.) was suspended in ultrapure water (Milli-Q water) to a concentration of 1% (w/v), and dissolved by stirring with heating at 90° C. Using this aqueous solution, DMEM/F-12 medium compositions having a final xanthan gum concentration of 0.1, 0.15 or 0.2% (w/v) were prepared. In addition, an aqueous solution containing 0.2% (w/v) κ-carageenan (GENUGEL WR-80-J, manufactured by SANSHO Co., Ltd.) and 0.2% (w/v) locust bean gum (GENUGUM RL-200-J, manufactured by SANSHO Co., Ltd.) was prepared by heating at 90° C. Using the aqueous solution, DMEM/F-12 medium (manufactured by Sigma Ltd.) compositions containing 0.03, 0.04 or 0.05% (w/v) K-carageenan and locust bean gum were prepared.

Figure 5:
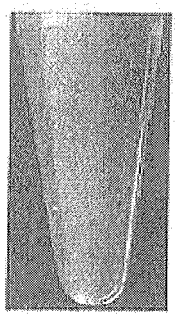
FIG. 5 is a Figure showing that, when spheres of HeLa cells were added to the medium composition, the spheres were uniformly dispersed and were in a suspended state.
Figure 5:

In the same manner as in Reference Experimental Example 2, spheres of HeLa cells were formed, and several tens of the spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that addition of an equal amount of the medium to the cell suspension and centrifugation (300 to 400 G, 5 min) thereof result in sedimentation and recovery of the spheres of HeLa cells. The suspended state of the spheres of HeLa cells cultured in the medium composition is each shown in FIG. 5. In addition, the viscosity measured in the same manner as in Analysis Example 1 is shown in Tables 7 and 8.

TABLE 7

| xanthan gum concentration % (w/v) | state | viscosity (mPa·s) | HeLa cell suspension/ sedimentation |
|---|---|---|---|
| 0.1 | liquid | 3.69 | Suspension |
| 0.15 | liquid | 5.46 | Suspension |
| 0.2 | liquid | 7.26 | Suspension |

TABLE 8

| κ-carageenan, locust bean gum concentration % (w/v) | state | viscosity (mPa·s) | HeLa cell suspension/sedimentation |
|---|---|---|---|
| 0.03 | liquid | 1.34 | Suspension |
| 0.04 | liquid | 1.55 | Suspension |
| 0.05 | liquid | 1.95 | Suspension |

Reference Experimental Example 5: Cell Suspension Test Using Medium Composition Filtered with Filter A DMEM/F-12 medium composition containing 0.015% deacylated gellan gum (KELCOGEL CG-LA, manufactured by SANSHO Co., Ltd.) was prepared in the same manner as in Reference Experimental Example 2. Successively, this medium composition (1 mL) was filtered through 70 μm filter or 40 μm filter (manufactured by BD Falcon), 30 μm filter or 20 μm filter (manufactured by AS ONE Corporation), 10 μm filter (manufactured by Partec), or 5 μm filter, 1.2 μm filter, 0.45 μm filter or 0.2 μm filter (manufactured by Sartorius Stedim Japan). Spheres of HepG2 cells prepared in the same manner as in Reference Experimental Example 2 were added by about several tens spheres to the above-mentioned filtrates and stood at 37° C. for 1 hr, and the suspended state of the sphere cells was visually observed. As a result, it was confirmed that the spheres of HepG2 cells are maintained in a suspended state in the medium composition passed through a filter of not less than 10 μm, but sedimented in the medium composition passed through a filter of less than 5 μm. Furthermore, it was confirmed that centrifugation at room temperature, 300 G, 5 min, or addition of an equal amount of the medium and centrifugation at room temperature, 200 G, 5 min, of HepG2 cell spheres in a suspended state result in sedimentation and recovery of the spheres.

Reference Experimental Example 6: Sphere Formation Test

Figure 6:
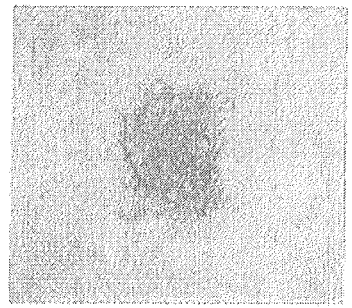
FIG. 6 is a Figure showing that spheres of HeLa cells could be formed in the medium composition.

In the same manner as in Reference Experimental Example 2, a composition of EMEM medium (manufactured by WAKO) containing 0.01% deacylated gellan gum (KELCOGEL CG-LA, manufactured by SANSHO Co., Ltd.) and 10% (v/v) fetal bovine serum was prepared. Successively, HeLa cells were added to a concentration of 1000 cells/mL, and dispensed to a 24-well plate (manufactured by Corning Incorporated). This plate was suspension-cultured by being stood still at 37° C. for 9 days, and formation of sphere was confirmed with a microscope. Furthermore, the sphere cells were sedimented by a centrifugation treatment (300 G, 5 min), and washed once with PBS (5 mL). A 100 μL trypsin-EDTA (ethylenediaminetetraacetic acid) solution (manufactured by WAKO) was added, and the mixture was incubated at 37° C. for 5 min. Here, to the obtained cell suspension (100 μL) was added EMEM medium (100 μL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HeLa cell increases to 170000 cells/mL. The sphere of HeLa cell formed in the medium composition is shown in FIG. 6.

Figure 7:
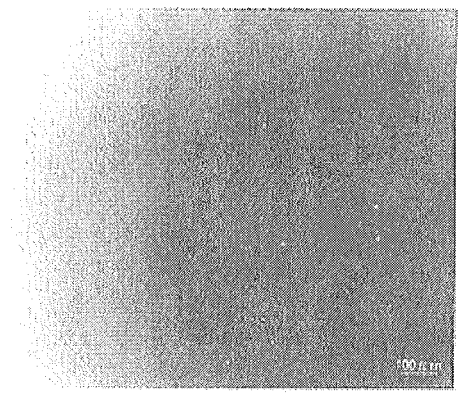
FIG. 7 is a Figure showing a film, which is one embodiment of the structure, wherein the concentration of the deacylated gellan gum in the medium composition was 0.02% (weight/volume).

Reference Experimental Example 7: Optical Microscope Observation of Structure Deacylated gellan gum (KELCOGEL CG-LA, manufactured by SANSHO Co., Ltd.) was suspended in pure water to 0.4% (w/v), and dissolved by stirring with heating at 90° C. DMEM/F-12 medium (manufactured by Aldrich, 95 mL) at a 2-fold concentration was placed in a 300 mL tall beaker, an aqueous deacylated gellan gum solution (5 mL) was added with stirring with a magnetic stirrer at room temperature, and the mixture was stirred as it was for 5 min to give a medium composition containing deacylated gellan gum at a final concentration of 0.02%. Furthermore, the medium composition was stirred by a homomixer (3000 rpm) for 5 min. The prepared medium composition was observed with an optical microscope (KEYENCE Corporation, BIOREVO BZ-9000). The observed structure is shown in FIG. 7.

Reference Experimental Example 8: Preparation by Mixing Heating Powder Medium and DAG Deacylated gellan gum (KELCOGEL CG-LA, manufactured by SANSHO Co., Ltd., 20 mg) and DMEM/F-12 medium (manufactured by Life Technologies, 1.58 g) were placed in a 200 mL Erlenmeyer flask, and pure water (100 mL) was poured therein. The mixture was sterilized at 121° C. for 20 min in an autoclave to prepare a DMEM/F-12 medium composition with a deacylated gellan gum concentration of 0.02%. To the prepared medium were added dextran beads Cytodex 1 (Size 200 μm, manufactured by GE Healthcare Life Sciences), and the dispersion state of the beads was confirmed by visual observation. For evaluation, a suspended state is ○, partial sedimentation/dispersed state is Δ, and sedimented state is x. The results are shown in Table 9.

TABLE 9

| deacylated gellan gum concentration % (w/v) | state | Cytodex1 dispersion |
|---|---|---|
| 0.05 | liquid | ○ |
| 0.02 | liquid | ○ |
| 0.01 | liquid | ○ |

Reference Experimental Example 9: Preparation of Medium Composition Containing Polysaccharides Xanthan gum (KELTROL CG, manufactured by SANSHO Co., Ltd.) was suspended in pure water to a concentration of 0.5% (w/v), and dissolved by stirring with heating at 90° C. Similarly, 0.5% (w/v) aqueous solutions of sodium alginate (Duck alginic acid NSPM, manufactured by FOOD CHEMIFA Co., Ltd.), locust bean gum (GENUGUM RL-200-J, manufactured by SANSHO Co., Ltd.), K-carageenan (GENUGEL WR-80-J, manufactured by SANSHO Co., Ltd.) or diutan gum (KELCO CRETE DG-F, manufactured by SANSHO Co., Ltd.) were prepared.

Each of the aqueous solutions and 0.2 or 0.1% (w/v) deacylated gellan gum solution and DMEM/F-12 medium at a 10-fold concentration were mixed, and the mixture was heated at 80° C. for 30 min, allowed to cool to room temperature, and 7.5% aqueous sodium hydrogen carbonate solution was added to prepare DMEM/F-12 medium compositions containing deacylated gellan gum at a final concentration of 0.01, 0.02% (w/v) and other polysaccharide at a final concentration of 0.1, 0.2, 0.3, 0.4% (w/v). In addition, a medium containing deacylated gellan gum was prepared as mentioned above, and a powder of methylcellulose (cP400, manufactured by WAKO) was added. The mixture was stirred in an ice bath to dissolve methylcellulose to prepare DMEM/F-12 medium compositions containing deacylated gellan gum at a final concentration of 0.01, 0.02% (w/v) and other methylcellulose at a final concentration of 0.1, 0.2, 0.3, 0.4% (w/v).

Polystyrene beads (Size 500-600 μm, manufactured by Polysciences Inc.) were added to the medium prepared above, and the dispersion state of the beads was confirmed by visual observation. For evaluation, a suspended state is ○, partial sedimentation/dispersed state is Δ, and sedimented state is x. The results are shown in Table 10.

TABLE 10

| deacylated gellan gum concentration % (w/v) | polysaccharide concentration % (w/v) | xanthan gum | alginic acid Na | locust bean gum | methyl-cellulose | κ-carageenan | diutan gum |
|---|---|---|---|---|---|---|---|
| 0.01 | 0.1 | ○ | ○ | ○ | X | ○ | ○ |
|  | 0.2 | ○ | ○ | ○ | Δ/X | solidified | not measured |
|  | 0.3 | ○ | ○ | ○ | Δ/X | solidified | not measured |
|  | 0.4 | ○ | ○ | ○ | Δ/X | solidified | not measured |
| 0.02 | 0.1 | ○ | ○ | ○ | ○/X | ○ | ○ |
|  | 0.2 | ○ | ○ | ○ | ○ | solidified | not measured |
|  | 0.3 | ○ | ○ | ○ | ○ | solidified | not measured |
|  | 0.4 | ○ | ○ | ○ | ○ | solidified | not measured |

Reference Experimental Example 10: Viscosity Measurement of Medium Composition Containing Polysaccharides By a method similar to that for the polysaccharide mixture of Reference Experimental Example 9, DMEM/F-12 media containing deacylated gellan gum at a final concentration of 0.005, 0.01% (w/v) and other polysaccharide were prepared. The final concentration of polysaccharide was set to 0.1% (w/v) for xanthan gum, sodium alginate, locust bean gum, 0.2% (w/v) for methylcellulose, and 0.05% (w/v) for K-carageenan and diutan gum. The state of each medium composition and the viscosity measured by a method similar to that in Analysis Example 1 are shown in Tables 11-16.

TABLE 11

| xanthan gum concentration % (w/v) | deacylated gellan gum concentration % (w/v) | state | viscosity (mPa · s) |
|---|---|---|---|
| 0.1 | 0.005 | liquid | 4.36 |
| 0.1 | 0.010 | liquid | 4.59 |

TABLE 12

| sodium alginate concentration % (w/v) | deacylated gellan gum concentration % (w/v) | state | viscosity (mPa · s) |
|---|---|---|---|
| 0.1 | 0.005 | liquid | 1.53 |
| 0.1 | 0.010 | liquid | 1.75 |

TABLE 13

| locust bean gum concentration % (w/v) | deacylated gellan gum concentration % (w/v) | state | viscosity (mPa · s) |
|---|---|---|---|
| 0.1 | 0.005 | liquid | 1.92 |
| 0.1 | 0.010 | liquid | 2.36 |

TABLE 14

| methylcellulose concentration % (w/v) | deacylated gellan gum concentration % (w/v) | state | viscosity (mPa · s) |
|---|---|---|---|
| 0.2 | 0.005 | liquid | 3.36 |
| 0.2 | 0.010 | liquid | 3.81 |

TABLE 15

| κ-carageenan concentration % (w/v) | deacylated gellan gum concentration % (w/v) | state | viscosity (mPa · s) |
|---|---|---|---|
| 0.05 | 0.005 | liquid | 1.04 |
| 0.05 | 0.010 | liquid | 1.28 |

TABLE 16

| diutan gum concentration % (w/v) | deacylated gellan gum concentration % (w/v) | state | viscosity (mPa · s) |
|---|---|---|---|
| 0.1 | 0.005 | liquid | 2.76 |
| 0.1 | 0.010 | liquid | 3.04 |

Reference Experimental Example 11: Preparation of Medium Composition with Changed Divalent Metal Ion Concentration Using DMEM/F-12 (D9785, manufactured by Aldrich) free of calcium chloride, magnesium sulfate and magnesium chloride and in the same manner as in the method of Reference Experimental Example 8, DMEM/F-12 medium composition containing 0.02% (w/v) deacylated gellan gum was prepared. DMEM/F-12 medium compositions added with calcium chloride or magnesium sulfate, and magnesium chloride such that the final concentration was set to the defined amount of DMEM/F-12 medium were prepared. In view of the defined composition of DMEM/F-12 medium, each final concentration was set to 0.116 g/L for calcium chloride, 0.049 g/L for magnesium sulfate, and 0.061 g/L for magnesium chloride.

To the prepared medium composition were added dextran beads Cytodex 1 (manufactured by GE Healthcare Life Sciences), and the dispersion state of the beads was confirmed 2 days later by visual observation. For evaluation, a suspended state is ○, partial sedimentation/dispersed state is Δ, and sedimented state is x. The results are shown in Table 17.

TABLE 17

| deacylated gellan gum concentration % (w/v) | calcium chloride | magnesium sulfate magnesium chloride | Cytodex1 dispersion |
|---|---|---|---|
| 0.02 | + | + | ○ |
| 0.02 | + | − | ○ |
| 0.02 | − | + | Δ |
| 0.02 | − | − | x |

Reference Experimental Example 12: Preparation of Medium Composition Later Added with Divalent Metal Cations A salt solution was prepared by dissolving 0.1% (w/v) deacylated gellan gum solution, a 5-fold concentration of DMEM/F-12 medium (not containing calcium chloride, magnesium sulfate and magnesium chloride, D9785, manufactured by Aldrich), calcium chloride (1167 mg), magnesium sulfate (489 mg) and magnesium chloride (287 mg) in pure water (300 mL). An aqueous deacylated gellan gum solution and pure water were placed in a 200 mL tall beaker, and the solution was stirred at 200 rpm using an anchor type stirring blade. Solution A, which is a mixture of the medium solution and water, was added, and the mixture was directly stirred for 10 min. Then, the salt solution was added, and 7.5% aqueous sodium hydrogen carbonate solution (1.6 mL) was further added to prepare DMEM/F-12 medium compositions containing deacylated gellan gum at a final concentration of 0.02%. The mixed amount of each solution is shown in the Table. After 4 hr from the preparation, 6 medium compositions were subjected to a dispersion evaluation of polystyrene beads and Cytodex1. The results are shown in Tables 18, 19.

TABLE 18

| | 0.1% (w/v) deacylated gellan gum aqueous solution | pure water | solution A | | salt solution |
|---|---|---|---|---|---|
| | | | 5-fold concentration DMEM/F-12 | pure water | calcium chloride magnesium chloride magnesium sulfate |
| 1 | 20 mL | 10 mL | 20 mL | 50 mL | none |
| 2 | 20 mL | 10 mL | 20 mL | 47 mL | 3 mL |
| 3 | 20 mL | 10 mL | 20 mL | 40 mL | 3 mL/water 7 mL |
| 4 | 20 mL | 30 mL | 20 mL | 30 mL | none |
| 5 | 20 mL | 30 mL | 20 mL | 27 mL | 3 mL |
| 6 | 20 mL | 30 mL | 20 mL | 20 mL | 3 mL/water 7 mL |

TABLE 19

| | deacylated gellan gum concentration % (w/v) | salt solution | polystyrene bead dispersion | Cytodex1 dispersion |
|---|---|---|---|---|
| 1 | 0.02 | − | x | x |
| 2 | 0.02 | + | ○ | ○ |
| 3 | 0.02 | + | ○ | ○ |
| 4 | 0.02 | − | x | x |
| 5 | 0.02 | + | ○ | ○ |
| 6 | 0.02 | + | ○ | ○ |

Reference Experimental Example 13: Preparation of Various Medium Compositions

A 0.1% (w/v) deacylated gellan gum solution and a medium solution having a high concentration were prepared. As a medium solution having a high concentration, MEM having a 10-fold concentration (M0268, manufactured by Aldrich), RPMI-1640 having a 10-fold concentration (R6504, manufactured by Aldrich) and DMEM having a 5-fold concentration (high-pressure sterilization corresponding medium, manufactured by Nissui) were prepared. A 0.1% (w/v) deacylated gellan gum solution, each high concentration medium, and pure water for adjusting concentration were mixed, and the mixture was heated at 80° C. for 30 min. The mixture was allowed to cool to room temperature, and 7.5% aqueous sodium hydrogen carbonate solution was added to prepare medium compositions containing deacylated gellan gum at a final concentration of 0.01, 0.02, 0.03% (w/v). The prepared 9 medium compositions were evaluated for the suspension and dispersion state of polystyrene beads and dextran beads Cytodex1, wherein a suspended state is ○, partial sedimentation/dispersed state is Δ, and sedimented state is x. The results are shown in Tables 20, 21.

TABLE 20

MEM medium

| deacylated gellan gum concentration % (w/v) | state | polystyrene bead dispersion | Cytodex1 dispersion |
|---|---|---|---|
| 0.01 | liquid | Δ | Δ |
| 0.02 | liquid | ○ | ○ |
| 0.03 | liquid | ○ | ○ |

TABLE 21

DMEM medium

| deacylated gellan gum concentration % (w/v) | state | polystyrene bead dispersion | Cytodex1 dispersion |
|---|---|---|---|
| 0.01 | liquid | Δ | Δ |
| 0.02 | liquid | ○ | ○ |
| 0.03 | liquid | ○ | ○ |

Reference Experimental Example 14: Particle Size Distribution Measurement of Medium Composition Containing Deacylated Gellan Gum According to Reference Example 1, DMEM/F-12 medium composition containing 0.038% (w/v) deacylated gellan gum was prepared. The medium was prepared by stirring at 3000 rpm or 6000 rpm for 1 min by a homomixer.

The particle size distribution of the medium composition was measured by Beckman Instruments Coulter, Inc. Multisizer 4 (precise particle size distribution measuring apparatus by Coulter principle) and the median size (d50) of the volume standard particle size distribution was determined. The results are shown in Table 22.

TABLE 22

| homomixer rotation number in medium preparation | d50 (μm) |
|---|---|
| 3000 rpm | 1.709 |
| 6000 rpm | 1.499 |

Reference Experimental Example 15: Phosphorylation of Deacylated Gellan Gum

Deacylated gellan gum (1 g) and pure water (40 mL) were measured off in a 100 mL glass test tube, and the mixture was heated at 100° C. for 30 min to prepare a suspension. To this suspension was added aqueous phosphoric acid solution (85%, 1 g), and the mixture was heated under reflux for 5 hr. Thereafter, it was allowed to cool to room temperature while stirring for 12 hr, and the obtained white suspension was poured into 99% ethanol (500 mL). The resulting floc white solid was collected by filtration and dried to give a pale-brown solid (0.4 g) as a phosphorylated substance of deacylated gellan gum. Introduction of a phosphate group was confirmed by Fourier-transform infrared spectroscopic analysis (manufactured by SHIMADZU CORPORATION, IR-Prestage 21) (1700 cm-1; P—OH, 1296 cm-1, 1265 cm-1; P═O). The pale-brown solid was decomposed by a micro wave heating digestion apparatus (ETHOS TC, manufactured by Milestone General), and the content of the phosphorus atom was measured by an inductively coupled plasma emission spectroscopic analyzer (ICP-OES) (SPS 5520, manufactured by SII NanoTechnology). The result was 3.5 wt % (n=2).

Reference Experimental Example 16: Preparation of Medium Composition Containing Phosphorylated Deacylated Gellan Gum An optional amount of phosphorylated deacylated gellan gum (30 mg) and DMEM/F-12 medium (manufactured by Life Technologies, 1.56 g) were placed in a 200 mL Erlenmeyer flask, and pure water (100 mL) was poured therein. The mixture was sterilized at 121° C. for 20 min in an autoclave to prepare a DMEM/F-12 medium composition having a deacylated gellan gum concentration of 0.03%. To the prepared medium were added dextran beads Cytodex 1 (manufactured by GE Healthcare Life Sciences), and the dispersion state of the beads was confirmed by visual observation. A dispersed state of the beads was found at a phosphorylated deacylated gellan gum concentration of 0.03% (w/v).

Reference Experimental Example 17: Preparation of Medium Composition Containing Deacylated Gellan Gum An aqueous deacylated gellan gum solution and a medium solution were mixed at the rates shown in the following Table to prepare a DMEM/F-12 medium composition having a deacylated gellan gum concentration of 0.02%, and the dispersion state of polystyrene beads (Size 500-600 μm, manufactured by Polysciences Inc.) was evaluated. The results are shown in Tables 23 and 24. By standing for 1 day or longer, the styrene beads were dispersed under all conditions.

TABLE 23

| deacylated gellan gum/pure water | DMEM/F12 powder medium/pure water | standing time |
|---|---|---|
| 20 mg/10 mL | 1.56 g/90 mL | 5 min |
| 20 mg/20 mL | 1.56 g/80 mL | 5 min |
| 20 mg/30 mL | 1.56 g/70 mL | 5 min |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |
| 20 mg/70 mL | 1.56 g/30 mL | 6 h |
| 20 mg/80 mL | 1.56 g/20 mL | 1 day |
| 20 mg/90 mL | 1.56 g/10 mL | 1 day |

"DMEM/F12 powder medium/pure water" was added to "deacylated gellan gum/pure water"

TABLE 24

| deacylated gellan gum/pure water | DMEM/F12 powder medium/pure water | standing time |
|---|---|---|
| 20 mg/10 mL | 1.56 g/90 mL | 5 min |
| 20 mg/20 mL | 1.56 g/80 mL | 5 min |
| 20 mg/30 mL | 1.56 g/70 mL | 1 h |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |
| 20 mg/70 mL | 1.56 g/30 mL | 1 day |
| 20 mg/80 mL | 1.56 g/20 mL | 1 day |
| 20 mg/90 mL | 1.56 g/10 mL | 1 day |

"Deacylated gellan gum/pure water" was added to "DMEM/F12 powder medium/pure water"

Reference Experimental Example 18: Preparation of Medium Composition Using Filter Deacylated gellan gum (KELCOGEL CG-LA, manufactured by SANSHO Co., Ltd.) was suspended in ultrapure water (Milli-Q water) to a final concentration of 0.02 or 0.04% (w/v), and dissolved by heating at 90° C. for 30 min or at 121° C. for 20 min. Furthermore, this aqueous solution (100 mL) was filtered with a polyethersulfone membrane filter having a pore size of 0.22 μm (manufactured by Corning Incorporated). Successively, this filtrate was mixed with a 2- to 4-fold concentration of DMEM/F-12 medium (manufactured by Sigma Aldrich), and the mixture was shaken by a mild mixer (SI-24, manufactured by TAITEC Co., Ltd.) for 1 hr to prepare medium compositions containing deacylated gellan gum at a final concentration of 0.01 or 0.015% (w/v) (e.g., 25 mL each of 0.02% (w/v) aqueous deacylated gellan gum solution and DMEM/F-12 medium having a 2-fold concentration were mixed to prepare 0.01% (w/v) deacylated gellan gum medium composition (50 mL)). By a method similar to that in Reference Experimental Example 2, spheres of HepG2 cells were formed, and several tens of the spheres were added to the medium (1 mL) prepared above, stood at 37° C., of the suspended state of the sphere cells was visually observed after 1 hr and one night. As a result, it was confirmed that the spheres of HepG2 cells are maintained in a suspended state in all of the above-mentioned medium composition. Furthermore, two-fold volume of the medium was added, and the cell suspension was centrifuged (500 G, 5 min). It was confirmed that the spheres of HepG2 cells are sedimented, and the cells can be recovered in all medium compositions. The dispersed state of the sphere after one night was confirmed by visual observation and evaluated, wherein a suspended and dispersed state is ○, partial sedimentation/dispersed state is Δ, and sedimented state is x. The evaluation results are shown in Table 25.

TABLE 25

| aqueous deacylated gellan gum solution concentration (%) | temperature (° C.) during dissolution | deacylated gellan gum concentration (%) of medium composition | suspending effect of HepG2 cells |
|---|---|---|---|
| 0.02 | 90 | 0.010 | ○ |
|  |  | 0.015 | ○ |
|  | 120 | 0.010 | ○ |
|  |  | 0.015 | ○ |
| 0.04 | 90 | 0.010 | ○ |
|  |  | 0.015 | ○ |
|  | 120 | 0.010 | ○ |
|  |  | 0.015 | ○ |

Reference Experimental Example 19: Cell Proliferation Test by Culturing Cell Line-Derived Sphere Human embryonic kidney cell line HEK293 (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 2 days in a $CO_2$ incubator (5% $CO_2$). A suspension (10 mL) of the spheres (diameter 100-200 μm) of HEK293 cells obtained here was centrifuged (200 G, 5 min) to allow for sphere sedimentation, the supernatant was removed and the sphere was suspended in 1 mL. Successively, the medium (10 mL) was added to the sphere suspension (200 μL, cell number about 200000) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to EMEM medium containing 10% (v/v) fetal bovine serum.

After static culture of the above-mentioned sphere suspension in a $CO_2$ incubator (5% $CO_2$) at 37° C. for 5 days, a two-fold volume of the medium was added. The mixture was centrifuged (500 G, 5 min) to allow for sphere sedimentation, and the supernatant was removed. Successively, the recovered m sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (500 G, 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.). As a control, a medium composition free of deacylated gellan gum was produced and a similar experiment was performed.

As a result, it was confirmed that, using the medium composition, the spheres of HEK293 cells can be cultivated in a suspended state, and the cells efficiently proliferate in the medium composition. Furthermore, the medium composition was confirmed to show a small rate of the dead cells as compared to a medium composition free of deacylated gellan gum when the cells were proliferated, and have a superior cell proliferation promoting effect. The sphere cultured in an existing medium sedimented on the bottom of the culture container.

The relative number of the HEK293 cells is shown in Table 26, wherein the number of the cells cultured in a medium free of deacylated gellan gum is 1. In addition, the relative rate of the dead cells is shown in Table 27, wherein the rate of the dead cells cultured in a medium free of deacylated gellan gum (dead cell number/viable cell number) is 1.

TABLE 26

| deacylated gellan gum |  | HEK293 cells |
|---|---|---|
| absent | relative cell number | 1.0 |
| present | relative cell number | 1.6 |

TABLE 27

| deacylated gellan gum |  | HEK293 cells |
|---|---|---|
| absent | relative dead cell rate | 1.0 |
| present | relative dead cell rate | 0.3 |

Reference Experimental Example 20: Cell Proliferation Test by Culturing Insect Cell Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to Sf-900 (registered trade mark) III SFM medium (manufactured by Gibco). Successively, *Spodoptera frugiperda* derived Sf9 cells (manufactured by Gibco) were inoculated to the above-mentioned medium composition added with deacylated gellan gum at 100000 cells/mL, and dispensed to the wells of a 24-well flat bottom microplate (manufactured by Corning Incorporated) at 1 mL/well. The cell suspensions were cultured by being stood still in an incubator at 25° C. for 5 days. Thereafter, a part of the culture medium was recovered, the same amount of Trypan Blue staining solution (manufactured by Invitrogen Corporation) was added, and the number of viable cells was measured by a hemocytometer (manufactured by ERMA INC.). As a control, a medium composition free of deacylated gellan gum was produced and subjected to a similar experiment.

As a result, it was confirmed that, using the medium composition, Sf9 cell can be uniformly cultivated in a suspended state, and proliferates in the medium composition. Furthermore, it was confirmed that the medium composition is superior in the effect of promoting cell proliferation when the cells is proliferated, as compared to a medium composition free of deacylated gellan gum. The cell number of Sf9 cells after suspension static culture for 5 days is shown in Table 28.

TABLE 28

| deacylated gellan gum | Sf9 cell number (×10000) |
|---|---|
| absent | 33.5 |
| present | 47.4 |

Reference Experimental Example 21: Cell Proliferation Test by Culturing CD34 Positive Cells Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v), 20 ng/mL thrombopoietin (manufactured by WAKO) and 100 ng/mL stem cell factor (SCF, manufactured by WAKO) to StemSpan SFEM medium (manufactured by StemCell Technologies). Successively, human cord blood-derived CD34 positive cells (manufactured by Lonza) were inoculated to the above-mentioned medium composition added with deacylated gellan gum to 10000 cells/mL, and dispensed to the wells of a 24-well flat bottom microplate (manufactured by Corning Incorporated) at 1 mL/well. The cell suspensions were subjected to static culture at 37° C. for 7 days in a $CO_2$ incubator (5% $CO_2$). Thereafter, a part of the culture medium was recovered, the same amount of Trypan Blue staining solution (manufactured by Invitrogen Corporation) was added, and the number of viable cells was measured by a hemocytometer (manufactured by ERMA INC.). A 3-fold volume of the medium was added to the culture medium and the mixture was centrifuged (500 G, 5 min) to allow for sedimentation of all cells. As a control, a medium composition free of deacylated gellan gum was produced and subjected to a similar experiment.

As a result, it was confirmed that, using the medium composition, CD34 positive cells can be uniformly cultivated in a suspended state, and proliferates in the medium composition. Furthermore, the medium composition was confirmed to show a cell proliferation promoting effect of the level equal to or more than that of the existing media without deacylated gellan gum. In addition, it was confirmed that centrifugation results in sedimentation of the cells and the cells can be recovered. The relative number of the cells proliferated from the CD34 positive cells after suspension static culture for 7 days, wherein the number of the cells cultured in a medium free of deacylated gellan gum is 1, is shown in Table 29.

TABLE 29

| deacylated gellan gum | relative cell number |
|---|---|
| absent | 1.0 |
| present | 1.2 |

Reference Experimental Example 22: Sphere Formation Test

Figure 8:
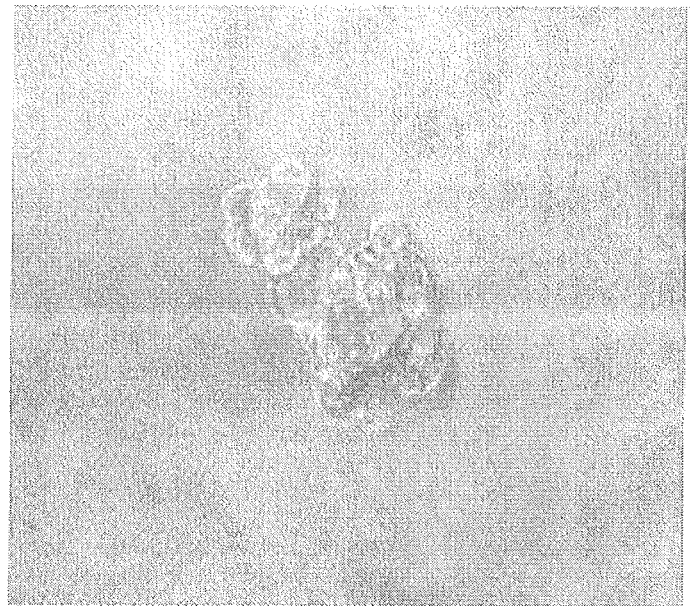
FIG. 8 is a Figure showing that spheres of HepG2 cells could be formed in the medium composition.

In the same manner as in Reference Experimental Example 2, a composition of DMEM medium (manufactured by WAKO) containing 0.015% deacylated gellan gum (KELCOGEL CG-LA, manufactured by SANSHO Co., Ltd.) and 10% (v/v) fetal bovine serum was prepared. Successively, HepG2 cells were added to a cell concentration of 15000 cells/mL, and dispensed by 1 mL to a 24-well plate (manufactured by Corning Incorporated). This plate was suspension-cultured by being stood still at 37° C. for 7 days, and formation of sphere was confirmed with a microscope. Furthermore, the sphere cells were sedimented by a centrifugation treatment (400 G, 5 min), and washed once with PBS (5 mL). A 100 µL trypsin-EDTA (ethylenediaminetetraacetic acid) solution (manufactured by WAKO) was added, and the mixture was incubated at 37° C. for 5 min. Here, to the obtained cell suspension (100 µL) was added DMEM medium (100 µL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HepG2 cells formed a sphere in the medium composition and increased to 80800 cells/mL. The sphere of HepG2 cells formed in the medium composition is shown in FIG. 8.

Reference Experimental Example 23: Cell Suspension Test Using Cell Line-Derived Sphere Diutan gum (KELKO-CRETE DG, manufactured by SANSHO Co., Ltd.) was suspended in ultrapure water (Milli-Q water) to a concentration of 0.3% (w/v), and dissolved by stirring with heating at 90° C. Using this aqueous solution, DMEM/F-12 medium compositions having a final diutan gum concentration of 0.1% (w/v) were prepared. In addition, an aqueous solution containing 0.5% (w/v) native-type gellan gum (KELCO gel HT, manufactured by San-Ei Gen F.F.I., Inc.) was prepared by heating at 90° C. Using the aqueous solution, DMEM/F-12 medium (manufactured by Sigma Ltd.) compositions containing 0.05 or 0.1% (w/v) native-type gellan gum was prepared.

In the same manner as in Reference Experimental Example 2, spheres of HeLa cells were produced, and several tens of spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that centrifugation (200 G, 5 min) of the cell suspension containing 0.1% (w/v) diutan gum result in sedimentation and recovery of the spheres of HeLa cells.

Reference Experimental Example 24: Cell Suspension Test Using Magnetic Beads Having Cell Adhesion Ability—1

A suspension of GEM (registered trade mark, Global Eukaryotic Microcarrier, manufactured by GL Sciences Inc.) coated with laminin or fibronectin was dispensed by 500 µL to a 1.5 mL volume micro test tube (manufactured by Eppendorf), GEM was accumulated from the above-mentioned GEM suspension by using a magnet stand (TA4899N12, manufactured by TAMAGAWA SEIKI CO., LTD.) and the solvent was removed. Furthermore, GEM was washed twice with DMEM medium (manufactured by WAKO, 500 µL) containing 10% (v/v) fetal bovine serum, and suspended in the same medium (500 µL). This suspension was dispensed to a Sumilon cell tight plate 24F (manufactured by SUMITOMO BAKELITE), which is a cell low adhesion plate, at 50 µL per 1 well. Successively, HepG2 cells prepared separately were added at 250000 cells/mL, and the final volume was adjusted with the same medium to 500 µL/well. This cell suspension was manually stirred, and the plate was stood overnight in a $CO_2$ incubator (5% $CO_2$). After confirmation of cell adhesion on GEM with a microscope, the cell suspension was transferred to a 1.5 mL micro test tube (manufactured by Eppendorf), cell-attached GEM was accumulated the above-mentioned magnet stand and the supernatant was removed.

By a method similar to that in Reference Experimental Example 2, a DMEM medium (manufactured by WAKO) composition containing 0.015% of deacylated gellan gum (KELCOGEL CG-LA, manufactured by SANSHO Co., Ltd.) and 10% (v/v) fetal bovine serum was prepared. This medium composition or the above medium free of deacylated gellan gum was each added by 1 mL to the HepG2 cell-attached GEM (laminin or fibronectin-coated) prepared above, suspended, and transferred to Sumilon cell tight plate 24F. Successively, this plate was stood for 6 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 µL of trypsin-EDTA (ethylenediaminetetraacetic acid) solution (manufactured by WAKO) was added, and the mixture was incubated at 37° C. for 10 min. To 200 µL of the cell suspension obtained here was added 800 µL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition, GEM adhered with HepG2 cells can be cultivated in a suspended state, and efficiently proliferates in the medium composition. Furthermore, it was confirmed that the medium composition shows a cell proliferation promoting effect superior to that of the existing media free of deacylated gellan gum. In addition, it was confirmed that, using magnetic force, HepG2 cell-attached GEM can be collected from the medium composition, and further, HepG2 cells can be recovered from this GEM.

Figure 9:
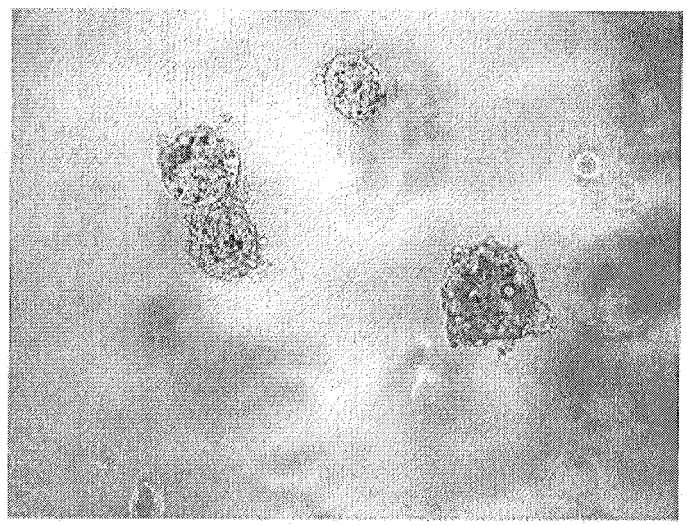
FIG. 9 is a Figure showing the suspended state of laminin-coated GEM attached with HepG2 cells, when it was cultured in the medium composition.

The cell number of HepG2 cells when cultured for 6 days on GEM in a deacylated gellan gum-containing or -free medium is shown in Table 30. In addition, the suspended state of HepG2 cell-attached laminin-coated GEM when cultured in the medium composition is shown in FIG. 9.

Reference Experimental Example 25: Cell Suspension Test Using Magnetic Beads Having Cell Adhesion Ability—2

In the same manner as in Reference Experimental Example 24, fibronectin-coated GEM (registered trade mark, Global Eukaryotic Microcarrier, manufactured by GL Sciences Inc.) was suspended in MF-Medium (registered trade mark) mesenchymal stem cell proliferation medium (manufactured by TOYOBO CO., LTD.). This suspension was dispensed to a Sumilon cell tight plate 24F (manufactured by SUMITOMO BAKELITE), which is a cell low adhesion plate, at 50 µL per 1 well. Successively, separately prepared human bone marrow-derived mesenchymal stem cell (manufactured by Cell Applications) was added at 250000 cells/mL and, in the same manner as in Reference Experimental Example 24, this plate was stood overnight in a $CO_2$ incubator (5% $CO_2$) to prepare GEM adhered with mesenchymal stem cells.

By a method similar to that in Reference Experimental Example 2, an MF-Medium (registered trade mark) mesenchymal stem cell proliferation medium (manufactured by TOYOBO CO., LTD.) composition containing 0.015% of deacylated gellan gum (KELCOGEL CG-LA, manufactured by SANSHO Co., Ltd.) was prepared. This medium composition or the above medium free of deacylated gellan gum was each added by 1 mL to the mesenchymal stem cell-attached GEM (fibronectin-coated) prepared above, suspended, and transferred to Sumilon cell tight plate 24F. Successively, this plate was stood for 4 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 µL of trypsin-EDTA (ethylenediaminetetraacetic acid) solution (manufactured by WAKO) was added, and the mixture was incubated at 37° C. for 10 min. To 200 µL of the cell suspension obtained here was added 800 µL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition, GEM adhered with mesenchymal stem cells can be cultivated in a suspended state, and efficiently proliferates in the medium composition. Furthermore, it was confirmed that the medium composition shows a cell proliferation promoting effect superior to that of the existing media without deacylated gellan gum. In addition, it was confirmed that, using magnetic force, mesenchymal stem cell-attached GEM can be collected from the medium composition, and further the mesenchymal stem cells can be recovered from this GEM.

The cell number of mesenchymal stem cells when cultured for 4 days on GEM in a deacylated gellan gum-containing or -free medium is shown in Table 31.

TABLE 30

| deacylated gellan gum | HepG2 cell number (×10000/mL) | |
| --- | --- | --- |
| | laminin coated GEM | fibronectin coated GEM |
| absent | 50.0 | 54.7 |
| present | 112.3 | 94.0 |

TABLE 31

| deacylated gellan gum | mesenchymal stem cell number (×10000/mL) |
| --- | --- |
| absent | 11.3 |
| present | 20.9 |

Reference Experimental Example 26: Cell Suspension Test Using Alginic Acid Bead The following test was performed according to the method of an alginic acid three-dimensional culture kit manufactured by PG Research. Separately prepared HepG2 cells were added to a sodium alginate solution (manufactured by PG research, 2.5 mL) at 400000 cells/mL, and human recombinant laminin 511 (manufactured by Veritas Ltd.) was further added at 5 μg/mL to prepare a cell suspension. The cell suspension was recovered with a 5 mL syringe (manufactured by TERUMO CORPORATION) having a gavage needle, and a 22 G injection needle (manufactured by TERUMO CORPORATION) was set to this syringe. Successively, the cell suspension was added by 10 drops to each well of a 24 well flat bottom microplate (manufactured by PG research) added with 2 mL each of an aqueous calcium chloride solution (manufactured by PG research). The mixture was stood for 10 min at room temperature, formation of alginic acid bead was confirmed, the calcium chloride solution was removed, PBS (2 mL) was added, and the mixture was stood at room temperature for 15 min. Furthermore, PBS was removed, DMEM medium (manufactured by WAKO, 2 mL) containing 10% (v/v) fetal bovine serum was added and the mixture was stood at room temperature for 15 min. The medium was removed, DMEM medium (manufactured by WAKO) composition containing 0.03% deacylated gellan gum (KELCOGEL CG-LA, manufactured by SANSHO Co., Ltd.) and 10% (v/v) fetal bovine serum, which was prepared by a method similar to that in Reference Experimental Example 2, or the above medium free of deacylated gellan gum was added by 1 mL to each well, and the mixture was subjected to static culture for 8 days in a $CO_2$ incubator (5% $CO_2$). The medium was exchanged on day 4 of culture.

The cultured alginic acid beads were transferred to a 1.5 mL micro test tube (manufactured by Eppendorf) using a 1 mL tip, a sodium citrate solution (1 mL, manufactured by PG research) was added to each tube, and the mixture was stirred at room temperature for 15 min to dissolve the alginic acid beads. Successively, cells were sedimented by centrifugation at 300 G for 3 min and the supernatant was removed. To the cells was added 200 μL of trypsin-EDTA (ethylenediaminetetraacetic acid) solution (manufactured by WAKO), and the mixture was incubated at 37° C. for 5 min. To the obtained cell suspension (200 μL) was added 800 μL of DMEM medium containing 10% (v/v) fetal bovine serum, and to a part of the cell suspension was added the same amount of Trypan Blue staining solution (manufactured by Invitrogen Corporation), and the number of the viable cells was measured by a hemocytometer (manufactured by ERMA INC.).

As a result, it was confirmed that, using the medium composition, alginic acid bead-embedded HepG2 cells can be cultivated in a suspended state, and efficiently proliferates in the medium composition. Furthermore, it was confirmed that the medium composition shows a cell proliferation promoting effect superior to that of the existing media without deacylated gellan gum.

Figure 10:
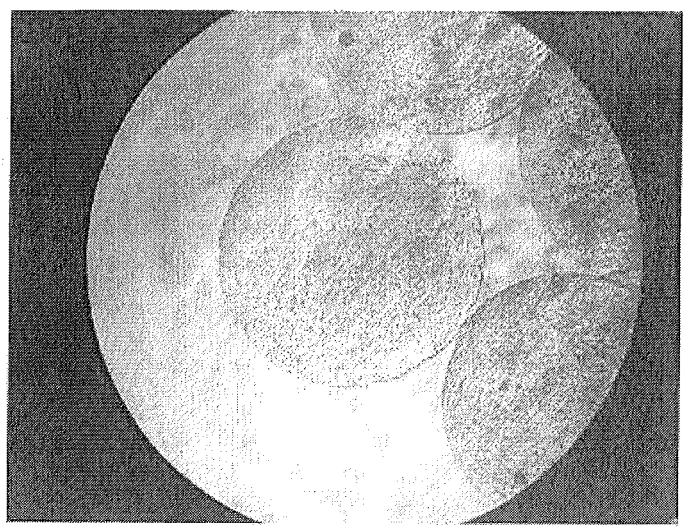
FIG. 10 is a Figure showing the suspended state of alginic acid beads in which HepG2 cells were embedded, when they were cultured in the medium composition.

The cell number of HepG2 cells when cultured in alginic acid beads in a deacylated gellan gum-containing or -free medium for 8 days is shown in Table 32. In addition, the suspended state when the HepG2 cell-embedded alginic acid beads were cultured in the medium composition is shown in FIG. 10.

TABLE 32

| deacylated gellan gum | HepG2 cell number (×10000/mL) |
|---|---|
| absent | 34.9 |
| present | 51.8 |

Reference Experimental Example 27: Cell Suspension Test Using Collagen Gel Capsule A: tissue culture collagen Cell matrix (registered trade mark) Type I-A (cell matrix, manufactured by Nitta Gelatin Inc.), B: 10-fold concentration of DMEM/F-12 medium (manufactured by Aldrich), C: reconstitution buffer (obtained by adding sodium hydrogen carbonate (2.2 g), HEPES (4-(2-hydroxyethyl)-1-piperazineethanesulfonic acid)) (4.77 g) to 0.05N sodium hydroxide solution (100 mL) and subjecting the mixture to filtration sterilization) were mixed at A:B:C=8:1:1 while cooling in ice. Furthermore, human recombinant laminin 511 (manufactured by Veritas Ltd.) was added at 5 μg/mL to prepare a collagen mixed solution (500 μL). To the mixed solution was added separately-prepared HepG2 cells at 200000 cell/mL, and the total amount was recovered using a 1.5 mL syringe (manufactured by TERUMO CORPORATION) with a 25 G injection needle (manufactured by TERUMO CORPORATION). Successively, the cell suspension was added dropwise by one drop to a flat bottom tube (manufactured by BM Equipment Co., Ltd.) containing DMEM medium (manufactured by WAKO) (10 mL) containing 10% (v/v) fetal bovine serum and incubated in advance at 37° C. using the above-mentioned syringe. The mixture was incubated in a water bath at 37° C. for 10 min and formation of an indeterminate collagen gel capsule with a diameter of about 2 mm was confirmed, deacylated gellan gum (KELCOGEL CG-LA, manufactured by SANSHO Co., Ltd.) was added at a final concentration of 0.04% by a method similar to that in Reference Experimental Example 2, and the above-mentioned capsule was suspended by gently stirring. Successively, the tube was subjected to static culture in a $CO_2$ incubator (5% $CO_2$) for 5 days.

PBS (25 mL) was added to a culture medium containing a collagen gel capsule, and the collagen gel capsule was sedimented by centrifugation at 400 G for 5 min and the supernatant was removed. Again, PBS (25 mL) was added, the mixture was centrifuged, and the supernatant was removed to make the amount of the rest 5 mL. To this solution was added 1% (W/V) collagenase L (manufactured by Nitta Gelatin Inc., 20 μL), and the mixture was shaken at 37° C. for 2 hr. After confirming dissolution of the collagen gel, PBS (10 mL) was added, and the cells were sedimented by centrifugation at 400 G for 5 min and the supernatant was removed. To the cells was added 1 mL of trypsin-EDTA (ethylenediaminetetraacetic acid) solution (manufactured by WAKO), and the mixture was incubated at 37° C. for 5 min. To the obtained cell suspension was added 4 mM of DMEM medium containing 10% (v/v) fetal bovine serum, and the cells were sedimented by centrifugation at 400 G for 5 min and the supernatant was removed. The obtained cells were suspended in 2 mL of the same medium above, and to a part thereof was added the same amount of Trypan Blue staining solution (manufactured by Invitrogen Corporation), and the number of the viable cells was measured by a hemocytometer (manufactured by ERMA INC.).

As a result, it was confirmed that, using the medium composition, collagen gel capsule embedded with HepG2 cells can be cultivated in a suspended state, and the cells efficiently proliferate in the medium composition. Furthermore, the medium composition was confirmed to show a cell proliferation promoting effect superior to that of the existing media without deacylated gellan gum.

Figure 11:
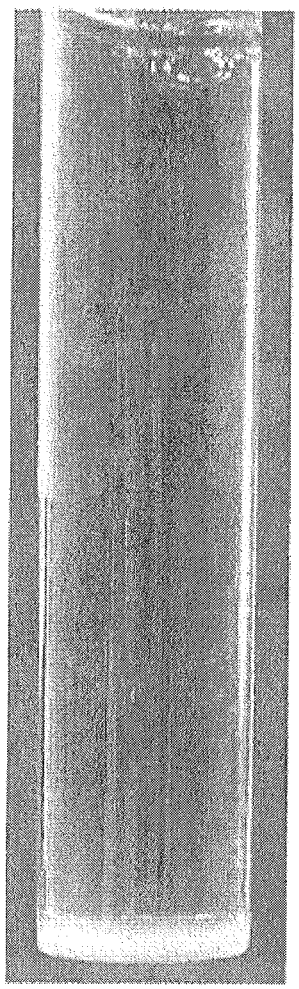
FIG. 11 is a Figure showing the suspended state of a collagen gel capsule in which HepG2 cells were embedded, when they were cultured in the medium composition.

The cell number of HepG2 cells when cultured in collagen gel capsule in a deacylated gellan gum-containing or -free medium for 5 days is shown in Table 33. In addition, the suspended state when the HepG2 cell-embedded collagen gel capsule was cultured in the medium composition is shown in FIG. 11.

TABLE 33

| deacylated gellan gum | HepG2 cell number (×10000/mL) |
|---|---|
| absent | 62.4 |
| present | 106.0 |

Reference Experimental Example 28: Sphere Recovery Test Using Filter

A DMEM medium (manufactured by WAKO) composition containing 0.015% deacylated gellan gum (KELCO-GEL CG-LA, manufactured by SANSHO Co., Ltd.) and 10% (v/v) fetal bovine serum was prepared by a method similar to that in Reference Experimental Example 2. In addition, as a control, the same medium free of deacylated gellan gum was prepared. HepG2 cell spheres were formed by a method similar to that in Reference Experimental Example 2, and added to the medium (1 mL) prepared above by 86000 cells, the mixture was stood at 37° C. for 1 hr, and the sphere cell suspension was visually observed. Furthermore, the cell suspension was added onto Cell Strainers (manufactured by Becton, Dickinson and Company) having a mesh size of 40 μm to trap the spheres on the filter. Successively, PBS (10 mL) was flowed from the backside of the filter to recover the spheres in a 15 mL tube, the spheres were sedimented by centrifugation at 300 G for 5 min. The supernatant was removed, 500 μL of trypsin-EDTA (ethylenediaminetetraacetic acid) solution (manufactured by WAKO) was added to the spheres, and the mixture was incubated at 37° C. for 5 min. To the obtained cell suspension was added a DMEM medium (1 mL) containing 10% (v/v) fetal bovine serum, to a part thereof was added the same amount of Trypan Blue staining solution (manufactured by Invitrogen Corporation), and the number of viable cells was measured by a hemocytometer (manufactured by ERMA INC.). As a result, the sphere of HepG2 cells was confirmed to maintain a suspended state in the above-mentioned medium composition. Furthermore, it was confirmed that the cells of HepG2 cell sphere can be recovered at a recovery rate equivalent to that of a medium free of deacylated gellan gum by a filter treatment of a sphere suspension containing 0.015% deacylated gellan gum. The relative number recovered from the medium containing deacylated gellan gum is shown in Table 34, wherein the number of the HepG2 cells recovered with a filter and using a medium free of deacylated gellan gum is 1.

TABLE 34

| deacylated gellan gum | relative HepG2 cell number |
|---|---|
| absent | 1.0 |
| present | 1.1 |

Reference Experimental Example 29: Cell Suspension Test of Sphere Using Combination Agent of Various Polysaccharides A DMEM/F-12 medium composition containing a combination of xanthan gum (KELTROL CG, manufactured by SANSHO Co., Ltd.), sodium alginate (Duck alginic acid NSPM, manufactured by FOOD CHEMIFA Co., Ltd.), locust bean gum (GENUGUM RL-200-J, manufactured by SANSHO Co., Ltd.), methylcellulose (cP400, manufactured by WAKO), κ-carageenan (GENUGEL WR-80-J, manufactured by SANSHO Co., Ltd.), pectin (GENU pectin LM-102AS, manufactured by SANSHO Co., Ltd.) or diutan gum (KELCO CRETE DG-F, manufactured by SANSHO Co., Ltd.), and deacylated gellan gum (KELCOGEL CG-LA, manufactured by SANSHO Co., Ltd.) was prepared by a method similar to that in Reference Experimental Example 9. In the same manner as in Reference Experimental Example 2, spheres of HepG2 cells were produced, and several tens of spheres were added to each medium (1 mL) prepared above, the mixture was stood still at 37° C. for 1 hr or one night, and the suspended state of the sphere cells was visually observed. As a result, it was confirmed that the spheres of HepG2 cells maintained the suspended state in any of the above-mentioned medium compositions. Furthermore, it was confirmed in all medium compositions that addition of a 2-fold amount of the medium and centrifugation (500 G, 5 min) of the cell suspension result in sedimentation and recovery of the spheres of HepG2 cells. The dispersion state of the sphere after one night was confirmed by visual observation, wherein a suspended and dispersed state is ○, partial sedimentation/dispersed state is Δ, and sedimented state is x. The evaluation results are shown in Table 35 and Table 36. In the Table, – shows not performed.

TABLE 35

| deacylated gellan gum concentration (%) | saccharides addition concentration (%) | methylcellulose | diutan gum |
|---|---|---|---|
| 0.005 | 0.05 | — | Δ |
|  | 0.2 | Δ | — |

TABLE 36

| deacylated gellan gum concentration (%) | saccharides addition concentration (%) | xanthan gum | sodium alginate | locust bean gum | methyl-cellulose | κ-carageenan | pectin | diutan gum |
|---|---|---|---|---|---|---|---|---|
| 0.01 | 0.05 | — | — | — | — | ○ | — | ○ |
|  | 0.1 | ○ | ○ | ○ | — | — | Δ | — |
|  | 0.2 | — | — | — | ○ | — | — | — |

Comparison of Dispersibility of Beads and Cells—1

The dispersion state of dextran bead Cytodex (registered trade mark) 1 (manufactured by GE Healthcare Life Sciences) and HeLa cell sphere was compared between deacylated gellan gum containing medium prepared above (Comparative Example) and a methylcellulose-containing medium. The results are shown in Table. Since the dispersion states of Cytodex1 and HeLa cell sphere correlate well, Cytodex1 can be used as a cell sphere model.

TABLE 37

| deacylgellan gum concentration %(w/v) | Cytodex1 suspension/ sedimentation | HeLa cell suspension/ sedimentation |
|---|---|---|
| 0.01 | suspension/partial sedimentation | suspension |
| 0.02 | suspension | suspension |
| 0.03 | suspension | suspension |
| 0.05 | suspension | suspension |

TABLE 38

| Methylcellulose %(w/v) | Cytodex1 suspension/ sedimentation | HeLa cell suspension/ sedimentation |
|---|---|---|
| 0.1 | sedimentation | sedimentation |
| 0.3 | sedimentation | sedimentation |
| 0.6 | sedimentation | sedimentation |
| 1.0 | sedimentation | sedimentation |

Comparison of Dispersibility of Beads and Cells—2

The dispersion state of polystyrene bead (Size 500-600 μm, manufactured by Polysciences Inc.) and HepG2 cell sphere was compared between the polysaccharide prepared in Reference Experimental Example 9 and deacylated gellan gum-containing medium. A suspended and dispersed state is ○, partial sedimentation/dispersed state is Δ, and sedimented state is x in the evaluation. The results are shown in Table. Since the dispersion states of polystyrene bead and HepG2 cell sphere correlate well, polystyrene bead can be used as a cell sphere model.

TABLE 39

| | polysaccharide concentration | xanthan gum | | alginic acid Na | | locust bean gum | | diutan gum | |
|---|---|---|---|---|---|---|---|---|---|
| | | PS bead | HepG2 mass | PS bead | HepG2 mass | PS bead | HepG2 mass | PS bead | HepG2 mass |
| deacylated gellan gum concentration 0.01% (w/v) | 0.05% | | | | | | | ○ | ○ |
| | 0.1% | ○ | ○ | ○ | ○ | ○ | ○ | ○ | |
| | 0.2% | ○ | | ○ | | ○ | | | |

Reference Experimental Example 30: Suspension Culture Test of Rice-Derived Plant Callus Fifty seeds of a fully ripe seed of rice Nipponbare selected with a salt solution (purchased from Koto agricultural cooperatives) were transferred to a 50 mL polystyrene tube (manufactured by BD Falcon), washed with sterilized water (50 mL), and stirred in 70% ethanol water (30 mL) for 1 min. Ethanol water was removed, Kitchen Haiter (manufactured by Kao Corporation, 30 mL) was added, and the mixture was stirred for 1 hr. Kitchen Haiter was removed, and washed 4 times with sterilized water (50 mL). The sterilized seeds were cultured on Murashige Skoog basal medium (M9274, manufactured by Sigma Aldrich) containing 2 μg/mL 2,4-dichlorophenoxyacetic acid (manufactured by Sigma Aldrich) and agar at 1.5 mL/well (24 well flat bottom microplate (manufactured by Corning Incorporated)). They were cultured under the conditions of 30° C., 16 hr dark place/8 hr dark place for 3 weeks, and cream-colored calluses (1-2 mm) grown on the seed blastocyst were harvested.

Figure 12:
FIG. 12 is a Figure showing the suspended state of rice-derived callus when cultured in the medium composition.

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.03% (w/v) to Murashige Skoog basal medium (M9274, manufactured by Sigma Aldrich) containing 2 μg/mL 2,4-dichlorophenoxyacetic acid (manufactured by Sigma Aldrich). 15 calluses prepared above were added to this medium composition in a 10 mL/flat bottom tube (manufactured by BM Equipment Co., Ltd.), and cultured with shaking at 25° C. for 7 days. As a result, it was confirmed that, using the medium composition, rice-derived callus can be cultivated in a suspended state, and the calluses are maintained in the medium composition. The suspended state is shown in FIG. 12 when the rice-derived callus was cultured in the medium composition.

Example 1: Preparation Method of Divalent Cation-Removed DAG (EDTA. 2Na Treatment NaOH Neutralization)

A suspension was made in a 300 mL recovery flask by adding deacylated gellan gum (KELCOGEL CG-LA, manufactured by SANSHO Co., Ltd.) (1.0 g), ethylenediaminetetraacetic acid disodium (manufactured by JUNSEI CHEMICAL CO., LTD.) (0.74 g), and pure water (200 mL), and heated in an oil bath set to 110° C. for 30 min. The mixture was allowed to cool to room temperature for 1 hr, and neutralized with 1N aqueous sodium hydroxide solution while confirming with pH test paper. The neutralized solution was added by small portions to a 500 mL beaker containing 200 mL of isopropylalcohol. The resulting suspending solid content was squeezed on a 58 μm mesh to remove water, and the obtained solid was dried in a vacuum oven set to 50° C. to give the object solid (0.86 g).

Example 2: Preparation Method of Divalent Cation-Removed DAG (EDTA.2Na Treatment KOH or LiOH Neutralization)

A suspension was made in a 300 mL recovery flask by adding deacylated gellan gum (KELCOGEL CG-LA, manufactured by SANSHO Co., Ltd.) (1.0 g), ethylenediaminetetraacetic acid disodium (manufactured by JUNSEI CHEMICAL CO., LTD.) (0.74 g), and pure water (200 mL), and heated in an oil bath set to 110° C. for 30 min. The mixture was allowed to cool to room temperature for 1 hr, and neutralized with 1N aqueous potassium hydroxide or lithium solution while confirming with pH test paper. The neutralized solution was added by small portions to a 500 mL beaker containing 200 mL of isopropylalcohol. The resulting suspending solid content was squeezed on a 58 μm mesh to remove water, and the obtained solid was dried in a vacuum oven set to 50° C. to give 0.88 g of white solid by neutralization with potassium hydroxide, and 1.04 g of white solid by neutralization with lithium hydroxide.

Example 3: Preparation Method of Divalent Cation-Removed DAG (Hydrogen Type Cation Exchange Resin, Batch Type)

A suspension was made in a 200 mL pear shape flask by adding deacylated gellan gum (KELCOGEL CG-LA, manufactured by SANSHO Co., Ltd.) (0.5 g), and pure water (100 mL), and heated in an oil bath set to 110° C. for 30 min. The suspension was allowed to cool to 50° C., cation exchange resin Dowex 50x8 (manufactured by The Dow Chemical Company) (10 g) was added, and the mixture was neutralized with aqueous potassium hydroxide solution while maintaining at not less than 50° C. The mixture was allowed to cool to room temperature over 1 hr. The neutralized solution was added by small portions to a 500 mL beaker containing 200 mL of isopropylalcohol. The resulting suspending solid content was squeezed on a 58 μm mesh to remove water, and the obtained solid was dried in a vacuum oven set to 50° C. to give the object solid (0.31 g).

Example 4: Preparation Method of Divalent Cation-Removed DAG (Sodium Type Cation Exchange Resin, Column Type)

A 0.5% aqueous deacylated gellan gum solution (50 mL) was flown through a column packed with an ion exchange resin (5 mL) over 1 hr. The ion exchange resins used were sodium type DOWEX 50Wx8 (The Dow Chemical Company), Sumichelate MC700 (manufactured by Sumika Chemtex Co., Ltd.), and Duolite C467 (manufactured by Sumika Chemtex Co., Ltd.). The eluate was added dropwise to 200 mL of isopropylalcohol, and the precipitated gel-like solid was collected by filtration. Water was removed by squeezing the resulting gel-like solid on a 58 μm mesh, and the obtained solid was dried in a vacuum oven set to 50° C. to give a white solid. Ultrapure water (2 mL) was added to the white solid (20 mg) such that the white solid concentration was 1%, and the mixture was subjected to a vortex treatment at room temperature (25° C.) for 1 hr, and solubility in water was examined. The yield of the white solid and the results of the dissolution test are shown below.

Metal Quantification Results of Duolite C467

A sample solution was appropriately diluted, and quantified by an inductively coupled plasma emission spectroscopic analyzer (ICP-OES; SPS 5520, manufactured by SII Nanotechnology).

TABLE 40

| | ppm (mg/Kg) | | | | | | | | | | | |
|---|---|---|---|---|---|---|---|---|---|---|---|---|
| | Al | Ca | Co | Cr | Cu | Fe | K | Mg | Mn | Na | Ni | Zn |
| before treatment | 100 | 3200 | <2 | <2 | <2 | 56 | 34000 | 1000 | 6 | 3600 | <2 | 2 |
| after treatment | 25 | 16 | <2 | 2 | <2 | 17 | 51 | 2 | <2 | 31000 | <2 | 7 |

TABLE 41

| solid yield | |
|---|---|
| ion exchange resin | yield |
| DOWEX 50Wx8 treatment | 184 mg |
| Sumichelate MC700 treatment | 205 mg |
| Duolite C467 treatment | 213 mg |

TABLE 42

| dissolution test | |
|---|---|
| ion exchange resin | dissolved/insoluble |
| untreated deacylated gellan gum | insoluble |
| DOWEX 50Wx8 treatment | dissolved |
| Sumichelate MC700 treatment | dissolved |
| Duolite C467 treatment | dissolved |

Example 5: Preparation Method of Divalent Cation-Removed DAG (Sodium Type Cation Exchange Resin, Batch Type)

A 0.5% aqueous deacylated gellan gum solution (200 mL) and Duolite C467 (5 mL) were added, and the mixture was stood at 70° C. for 24 hr with occasional stirring. Duolite C467 was removed by suction filtration, and the filtrate was added dropwise to isopropylalcohol. The precipitated gel-like solid was collected by filtration, and dried in vacuo at 50° C. Ultrapure water (2 mL) was added to the white solid (20 mg) such that the white solid concentration was 1%, and the mixture was subjected to a vortex treatment at room temperature (25° C.) for 30 min. As a result, the mixture was dissolved.

Metal Quantification Results of Duolite C467

A sample solution was appropriately diluted, and quantified by an inductively coupled plasma emission spectroscopic analyzer (ICP-OES; SPS 5520, manufactured by SII Nanotechnology).

TABLE 43

| | ppm (mg/Kg) | | | | | | | | | | | |
|---|---|---|---|---|---|---|---|---|---|---|---|---|
| | Al | Ca | Co | Cr | Cu | Fe | K | Mg | Mn | Na | Ni | Zn |
| before treatment | 100 | 3200 | <2 | <2 | <2 | 56 | 34000 | 1000 | 6 | 3600 | <2 | 2 |
| after treatment | 32 | 300 | <2 | <2 | <2 | 10.2 | 14000 | 148 | <2 | 32000 | <2 | <2 |

Example 6: Preparation Method of Divalent Cation-Removed DAG (Sodium Type Cation Exchange Resin, Column Type, Drying by Spray Dry Method)

Deacylated gellan gum (KELCOGEL CG-LA, manufactured by SANSHO Co., Ltd.) (25 g) and ion exchange water (4975 mL) were placed in a beaker, and dissolved by heating at 95° C. to give a 0.5% deacylated gellan gum solution. The deacylated gellan gum solution was passed through a column packed with Duolite C467 (trade name: manufactured by Sumika Chemtex Co., Ltd.) (500 ml) at a flow rate of 80 ml/min. The eluate was spray-dried by spray dry FOC-20-LS type (manufactured by OHKAWARA KAKOHKI CO., LTD.) to give a spherical powder. In this case, the deacylated gellan gum solution was supplied at 10 kg/h, the atomizer rotation number was 10,000-22,000 rpm, and drying air temperature was 130° C. The measurement was performed by a laser diffraction scattering method particle size distribution analyzer (LS13 320: manufactured by Beckman Instruments Coulter) to find that the particle size d50 of the powder was 7-12 µm.

Example 7: Production of DMEM Medium Using the Above-Mentioned DAG (Sterilization by Filtration)

Deacylated gellan gum (17 mg) after the treatment in Example 1 was dissolved in pure water (100 mL) at room temperature (25° C.). This solution was sterilized with a sterilization filter (pore size 0.22 µm). On the other hand, to a powder medium of DMEM (Life Technologies, Inc.) and sodium hydrogen carbonate was added pure water in an amount of one-tenth of the recommended level on preparation of the medium to prepare 10 m of an aqueous solution at a 10-fold concentration, and the solution was sterilized with a sterilization filter (pore size 0.22 µm). The deacylated gellan gum solution (90 mL) sterilized earlier was measured in a sterilized medium bottle, the DMEM medium having the 10-fold concentration was added, and the bottle was shaken and the mixture was thoroughly mixed, whereby the object DMEM medium (100 mL) having a deacylated gellan gum concentration of 0.015% (w/v) was prepared.

Example 8: Production of DMEM Medium Using the Above-Mentioned DAG (Autoclave Sterilization)

Deacylated gellan gum (300 mg) after the treatment in Example 2 was dissolved in pure water (20 mL) at room temperature (25° C.) and sterilized in an autoclave (121° C., 20 min). RPMI1640 liquid medium (Life Technologies, Inc.) (198 mL) was placed in a 500 mL tall beaker, and the earlier aqueous deacylated gellan gum solution (2 mL) after the autoclave treatment was added with vigorous stirring (3000 rpm) in a homomixer. The mixture was further stirred in a homomixer at 3000 rpm for 1 min, whereby the object RPMI1640 medium (202 mL) having a deacylated gellan gum concentration of 0.015% (w/v) was prepared.

Example 9: Cell Proliferation Test of Dispersed A549 Cells

Each divalent cation-removed deacylated gellan gum prepared in Examples 1 and 2 was suspended in ultrapure water (Milli-Q water) at 0.3% (w/v), and dissolved by heating at 37° C. Then, it was sterilized by filtration with a 0.22 µm diameter filter (manufactured by Millipore).

The solution was added to DMEM medium (manufactured by WAKO) containing 10% (v/v) fetal bovine serum, and blended by pipetting, whereby a medium composition added with the above-mentioned deacylated gellan gum and having a final concentration of 0.015% (w/v) was prepared. Successively, human lung cancer cell line A549 (manufactured by DS PHARMA BIOMEDICAL CO., LTD.) was seeded in the above-mentioned medium composition at 20000 cells/mL and dispensed to the wells of a 96 well flat bottom Ultra-Low Attachment Surface microplate (manufactured by Corning Incorporated, #3474) at 100 µL per well. As a comparison target, A549 cells were suspended in a medium composition added with the same concentration of deacylated gellan gum without a divalent ion removal treatment and the suspension was dispensed. As a negative control, A549 cells were suspended in the above medium free of deacylated gellan gum and the suspension was dispensed. Successively, the plate was cultured by being stood still in a $CO_2$ incubator (37° C., 5% $CO_2$) for 5 days. After culturing for 5 days, to the culture medium was added a WST-8 solution (manufactured by DOJINDO Laboratories, 20 µL), and the mixture was incubated at 37° C. for 100 min. The absorbance at 450 nm was measured by an absorbance spectrometer (manufactured by Molecular Devices, SPECTRA MAX 190), and the number of viable cells was measured by subtracting the absorbance of the medium alone.

As a result, it was confirmed that, using the medium composition of the present invention, A549 cells can be cultivated in a uniformly dispersed state without forming a cell aggregate having an excessive size, and efficiently proliferate in the medium composition. In this case, a difference in the effect on the cell proliferation was not found between divalent ion-removed deacylated gellan gum and non-treated deacylated gellan gum. The absorbance at 450 nm (corresponding to the number of A549 cells) 5 days after standing culture is shown in Table 44, In addition, cell aggregate mass was observed under an optical microscope (manufactured by OLYMPUS, CK30-F100), and the results evaluating suspended and dispersed state as ○, and sedimented state as x are shown in Table 44.

TABLE 44

|  | negative target | non-treated deacylated gellan gum | sodium type deacylated gellan gum | potassium type deacylated gellan gum |
| --- | --- | --- | --- | --- |
| cell number (absorbance) | 0.624 | 2.259 | 2.948 | 2.929 |
| suspended and dispersed state | x | ○ | ○ | ○ |

Example 10: Cell Proliferation Test of Dispersed A549 Cells

Each divalent cation-removed deacylated gellan gum prepared in Example 4 (Duolite C467 treatment) was suspended in ultrapure water (Milli-Q water) at 0.3% (w/v), dissolved by stirring with a stirrer at 25° C., and sterilized by filtration with a 0.22 μm diameter filter (manufactured by Millipore). The solution was added to DMEM medium (manufactured by WAKO) containing 10% (v/v) fetal bovine serum, and blended by pipetting, whereby a medium composition added with the above-mentioned deacylated gellan gum and having a final concentration of 0.015% (w/v) was prepared. Successively, human lung cancer cell line A549 (manufactured by DS PHARMA BIOMEDICAL CO., LTD.) was seeded in the above-mentioned medium composition at 100000 cells/mL and dispensed to the wells of a 96 well flat bottom Ultra-Low Attachment Surface microplate (manufactured by Corning Incorporated, #3474) at 100 μL per well. As a comparison target, A549 cells were suspended in a medium composition added with the same concentration of deacylated gellan gum without a divalent ion removal treatment and the suspension was dispensed. As a negative control, A549 cells were suspended in the above medium free of deacylated gellan gum and the suspension was dispensed. Successively, the plate was cultured by being stood still in a $CO_2$ incubator (37° C., 5% $CO_2$) for 6 days. After culturing for 6 days, to the culture medium was added an ATP measurement reagent (CellTiter-Glo (trade mark), manufactured by Promega Corporation, 100 μL), and the mixture was incubated at 25° C. for 15 min. The luminescence amount (RLU) was measured by Multiplate reader (manufactured by Molecular Devices, FlexStation 3), and RLU of medium alone was subtracted to count the viable cells.

As a result, it was confirmed that, using the medium composition of the present invention, A549 cells can be cultivated in a uniformly dispersed state without forming a cell aggregate having an excessive size, and efficiently proliferate in the medium composition. In this case, a difference in the effect on the cell proliferation was not found between divalent cation-removed deacylated gellan gum and non-treated deacylated gellan gum. The RLU (corresponding to the number of A549 cells) 6 days after standing culture is shown in Table 45.

TABLE 45

|  | negative target | non-treatment deacylated gellan gum | divalent cation-removed deacylated gellan gum |
| --- | --- | --- | --- |
| cell number (RLU) | 25404 | 84614 | 79779 |
| suspended and dispersed state | x | ○ | ○ |

Example 11: Production of Medium Composition Using the Above-Mentioned DAG and Other Polysaccharides Xanthan gum (San-Ace NXG-C, manufactured by San-Ei Gen Co. Ltd.) was suspended in pure water to a concentration of 0.5% (w/v), and dissolved by stirring with heating at 90° C. Similarly, 0.5% (w/v) aqueous solution of guar gum (Bistop D-2029, manufactured by San-Ei Gen Co. Ltd.) was prepared. This aqueous solution and 0.2 or 0.1% (w/v) DAG treated with a divalent cation removal treatment, DMEM/F-12 medium at a 10-fold concentration, and water for concentration adjustment were mixed, and the mixture was heated at 80° C. for 30 min, allowed to cool to room temperature, and 7.5% aqueous sodium hydrogen carbonate solution was added to prepare DMEM/F-12 medium compositions containing deacylated gellan gum at a final concentration of 0.01, 0.02% (w/v) and other polysaccharide at a final concentration of 0.1, 0.2, 0.3, 0.4% (w/v).

Example 12: Bead Dispersion Test

Polystyrene beads (size 500-600 μm, manufactured by Polysciences Inc.) were added to the medium prepared in Example 11, and the dispersion state of the beads was confirmed by visual observation. For evaluation, a suspended and dispersed state is ○, partial sedimentation/dispersed state is Δ, and sedimented state is x.

TABLE 46

| divalent cation-removed DAG concentration %(w/v) | polysaccharide concentration %(w/v) | xanthan gum | guar gum |
| --- | --- | --- | --- |
| 0.01 | 0.1 | ○ | x |
|  | 0.2 | ○ | Δ |
|  | 0.3 | ○ | ○ |
|  | 0.4 | ○ | ○ |
| 0.02 | 0.1 | ○ | ○ |
|  | 0.2 | ○ | ○ |
|  | 0.3 | ○ | ○ |
|  | 0.4 | ○ | ○ |

Comparative Example 1: Production Method of Medium Using Untreated DAG (Sterilization by Filtration)

Production of Deacylated Gellan Gum-Containing DMEM/Ham's F12 Medium

Deacylated gellan gum (KELCOGEL CG-LA, manufactured by SANSHO Co., Ltd.) (120 mg) was suspended in pure water (72 mL), and dissolved by stirring with heating at 90° C. for 1 hr. Thereto was added pure water to prepare a solution (720 mL) containing 0.017% (w/v) deacylated gellan gum, and the mixture was sterilized with a sterilization filter (pore size 0.22 µm). On the other hand, to a powder medium of a mixture of equal amounts of DMEM/Ham's F12 (Life Technologies, Inc.) and sodium hydrogen carbonate was added pure water in an amount of one-tenth of the recommended level on preparation of the medium to prepare 80 mL of an aqueous solution at a 10-fold concentration, and the solution was sterilized with a sterilization filter (pore size 0.22 µm). These were mixed with stirring under sterilization conditions at 25° C., whereby the object medium (800 mL) having a deacylated gellan gum concentration of 0.015% (w/v) was prepared.

Comparative Example 2: Production Method of Medium Using Untreated DAG (Autoclave Sterilization)

Production of Deacylated Gellan Gum-Containing DMEM/Ham's F12 Medium

Deacylated gellan gum (KELCOGEL CG-LA, manufactured by SANSHO Co., Ltd.) (0.30 g) was suspended in pure water (200 mL), and sterilized by heating in an autoclave (121° C., 20 min) to prepare an aqueous solution having a deacylated gellan gum concentration of 0.015% (w/v). To a powder medium of a mixture of equal amounts of DMEM/Ham's F12 (Life Technologies, Inc.) and sodium hydrogen carbonate was added pure water in an amount corresponding to 90% of the recommended level on preparation of the medium to prepare a liquid medium (180 mL) at a rather high concentration, and the medium was sterilized with a sterilization filter (pore size 0.22 µm). The aqueous deacylated gellan gum solution (20 mL) prepared earlier was added for about 10 sec while vigorously stirring the mixture in a homomixer (3000 rpm), and the mixture was further mixed with stirring at 3000 rpm for 1 min, whereby the medium (200 mL) having a deacylated gellan gum concentration of 0.015% (w/v) was prepared.

Example 13: Preparation Method of Divalent Cation-Removed DAG (Sodium Type Cation Exchange Resin, Batch Type, Simultaneous Progress of Dissolution of DAG and Treatment with Cation Exchange Resin)

Deacylated gellan gum (CG-LA, SANSHO Co., Ltd.) (1.0 g) and pure water (200 mL), and chelate resin Duolite C467(Na) (Sumika Chemtex Co., Ltd.) (4 mL) were placed in a 300 mL four-mouthed flask such that the deacylated gellan gum concentration was 0.5% (w/v). The mixture was heated to 70° C., and stirred with a tornado stirrer at 100 rpm for 1 hr. Then, the resin was filtered off with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder. A similar operation was performed by setting the temperature for stirring to 50° C., 30° C., 23° C., 10° C. to give a white solid.

Example 14: Preparation Method of Divalent Cation-Removed DAG When DAG Concentration was Increased (Sodium Type Cation Exchange Resin, Batch Type, Simultaneous Progress of Dissolution of DAG and Treatment with Cation Exchange Resin)

Deacylated gellan gum (CG-LA, SANSHO Co., Ltd.) (2.0 g) and pure water (200 mL), and chelate resin Duolite C467(Na) (Sumika Chemtex Co., Ltd.) (4 mL) were placed in a 300 mL four-mouthed flask such that the deacylated gellan gum concentration was 1% (w/v). The mixture was heated to 70° C., and stirred with a mechanical stirrer at 100 rpm for 1 hr. Then, the resin was filtered off with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder. A similar operation was performed by setting the amount of deacylated gellan gum to 4.0 g to give a white solid.

Example 15: Preparation Method of Divalent Cation-Removed DAG When the Amount of Resin to be Used was Increased (Sodium Type Cation Exchange Resin, Batch Type, Simultaneous Progress of Dissolution of DAG and Treatment with Cation Exchange Resin)

Deacylated gellan gum (CG-LA, SANSHO Co., Ltd.) (4.0 g) and pure water (200 mL), and chelate resin Duolite C467(Na) (Sumika Chemtex Co., Ltd.) (8 mL) were placed in a 300 mL four-mouthed flask such that the deacylated gellan gum concentration was 2% (w/v). The mixture was heated to 70° C., and stirred with a mechanical stirrer at 100 rpm for 1 hr. Then, the resin was filtered off with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder. A similar operation was performed by setting the amount of deacylated gellan gum to 5.0 g to give a white solid.

Example 16: Preparation Method of Divalent Cation-Removed DAG when the Amount of Resin to be Used was Decreased (Sodium Type Cation Exchange Resin, Batch Type, Simultaneous Progress of Dissolution of DAG and Treatment with Cation Exchange Resin)

Deacylated gellan gum (CG-LA, SANSHO Co., Ltd.) (2.0 g) and pure water (200 mL), and chelate resin Duolite C467(Na) (Sumika Chemtex Co., Ltd.) (1 mL) were placed in a 300 mL four-mouthed flask such that the deacylated gellan gum concentration was 1.0% (w/v). The mixture was heated to 70° C., and stirred with a mechanical stirrer at 100 rpm for 1 hr. Then, the resin was filtered off with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder.

Example 17: Preparation Method of Divalent Cation-Removed DAG When the Treatment Time with Resin was Extended (Sodium Type Cation Exchange Resin, Batch Type, Simultaneous Progress of Dissolution of DAG and Treatment with Cation Exchange Resin)

Deacylated gellan gum (CG-LA, SANSHO Co., Ltd.) (1.0 g) and pure water (200 mL), and chelate resin Duolite C467(Na) (Sumika Chemtex Co., Ltd.) (8 mL) were placed in a 300 mL four-mouthed flask such that the deacylated gellan gum concentration was 1.0% (w/v). The mixture was stirred with a mechanical stirrer at 23° C., 100 rpm for 5 hr. Then, the resin was filtered off with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder.

Comparative Example 3

Deacylated gellan gum (CG-LA, SANSHO Co., Ltd.) (1.0 g) and pure water (200 mL) were placed in a 300 mL four-mouthed flask such that the deacylated gellan gum concentration was 0.5% (w/v). The mixture was heated to 100° C. and stirred with a mechanical stirrer at 100 rpm for 1 hr. Then, the mixture was filtered with a filter paper (No. 5B, Kiriyama glass Co.), and the filtrate was poured into 500 mL of isopropylalcohol. The precipitated fiber-like solid was recovered, and dried in vacuo at 50° C. Then, the mixture was pulverized in a mixer to give a white powder.

Comparative Example 4

Deacylated gellan gum (CG-LA, SANSHO Co., Ltd.) (1.0 g) and pure water (200 mL), and strong acidic cation exchange resin (Htype) DOWEX™ (The Dow Chemical Company) (4 mL) were placed in a 300 mL four-mouthed flask such that the deacylated gellan gum concentration was 0.5% (w/v). The mixture was heated to 100° C. and stirred with a mechanical stirrer at 100 rpm for 1 hr. Then, the resin was filtered off with a filter paper (No. 5B, Kiriyama glass Co.), and the filtrate was poured into 500 mL of isopropylalcohol. However, a solid was not precipitated.

Comparative Example 5

Deacylated gellan gum (CG-LA, SANSHO Co., Ltd.) (1.0 g) and pure water (200 mL), and strong acidic cation exchange resin (H type) DOWEX™ (The Dow Chemical Company) (4 mL) were placed in a 300 mL four-mouthed flask such that the deacylated gellan gum concentration was 0.5% (w/v). The mixture was heated to 23° C. and stirred with a mechanical stirrer at 100 rpm for 1 hr. Then, the resin was filtered off with a filter paper (No. 5B, Kiriyama glass Co.); however, the filter paper was clogged and the filtration operation could not be completed.

The yields in Examples 13 to 17, and Comparative Examples 3 to 5 are shown below.

TABLE 47

| | conditions | yield |
|---|---|---|
| Example 13-1 | DAG 0.5% - 10° C., resin 4 mL | 0.89 g |
| Example 13-2 | DAG 0.5% - 23° C., resin 4 mL | 0.90 g |
| Example 13-3 | DAG 0.5% - 30° C., resin 4 mL | 0.90 g |
| Example 13-4 | DAG 0.5% - 50° C., resin 4 mL | 0.86 g |
| Example 13-5 | DAG 0.5% - 70° C., resin 4 mL | 0.82 g |
| Example 14-1 | DAG 1.0% - 70° C., resin 4 mL | 1.85 g |
| Example 14-2 | DAG 2.0% - 70° C., resin 4 mL | 3.76 g |
| Example 15-1 | DAG 2.0% - 70° C., resin 8 mL | 3.76 g |
| Example 15-2 | DAG 2.5% - 70° C., resin 8 mL | 4.51 g |
| Example 16 | DAG 1.0% - 70° C., resin 1 mL | 1.77 g |
| Example 17 | DAG 1.0% - 23° C., resin 8 mL | 1.60 g |
| Comparative Example 3 | DAG 0.5% - 100° C., no resin | 0.90 g |
| Comparative Example 4 | DAG 0.5% - 70° C., H type resin 4 mL | unrecoverable |
| Comparative Example 5 | DAG 0.5% - 23° C., H type resin 4 mL | unrecoverable |

Dissolution Test

DAG powders obtained by respective treatments in Examples 13 to 17, and Comparative Example 3 were examined for solubility in water at room temperature. Each powder (20 mg) and pure water (2 mL) were placed in a screwbottle (No. 1, Maruemu corporation), and they were stirred by vortex at room temperature for 1 hr. The solubility was confirmed by visual observation. The results are shown below.

TABLE 48

| | conditions | dissolved/insoluble |
|---|---|---|
| Example 13-1 | DAG 0.5% - 10° C., resin 4 mL | dissolved |
| Example 13-2 | DAG 0.5% - 23° C., resin 4 mL | dissolved |
| Example 13-3 | DAG 0.5% - 30° C., resin 4 mL | dissolved |
| Example 13-4 | DAG 0.5% - 50° C., resin 4 mL | dissolved |
| Example 13-5 | DAG 0.5% - 70° C., resin 4 mL | dissolved |
| Example 14-1 | DAG 1.0% - 70° C., resin 4 mL | dissolved |
| Example 14-2 | DAG 2.0% - 70° C., resin 4 mL | dissolved |
| Example 15-1 | DAG 2.0% - 70° C., resin 8 mL | dissolved |
| Example 15-2 | DAG 2.5% - 70° C., resin 8 mL | dissolved |
| Example 16 | DAG 1.0% - 70° C., resin 1 mL | dissolved |
| Example 17 | DAG 1.0% - 23° C., resin 8 mL | dissolved |
| Comparative Example 3 | DAG 0.5% - 100° C., no resin | insoluble |

Metal Quantification

DAG powders obtained by respective treatments in Examples 13 to 17, and Comparative Example 3 were added with an acid, thermally decomposed, and appropriately diluted with ultrapure water. The solutions were analyzed by an inductively coupled plasma emission spectroscopic analyzer (ICP-OES) (SPS 5520, SII Nanotechnology). The results are shown below.

TABLE 49

| | Al | Ca | Fe | K | Mg | Mn | Na | Zn |
|---|---|---|---|---|---|---|---|---|
| | | | | ppm | | | | |
| Example 13-1 | 7.1 | 620 | 16 | 8100 | 66 | 2.5 | 11000 | <2 |
| Example 13-2 | 30 | 710 | 29 | 11000 | 220 | 3.6 | 20000 | 2.3 |
| Example 13-3 | 7 | 27 | 15 | 8300 | 4 | <2 | 15000 | <2 |
| Example 13-4 | 11 | 20 | 12 | 7900 | 3 | <2 | 15000 | 4 |
| Example 13-5 | 8 | 19 | 11 | 8000 | 2 | <2 | 15000 | 5 |
| Example 14-1 | 5 | 17 | 7 | 11000 | 2 | <2 | 12000 | 7 |
| Example 14-2 | 23 | 90 | 6.8 | 24000 | 48 | <2 | 17000 | <2 |
| Example 15-1 | 41 | 14 | 3.4 | 18000 | 3.9 | <2 | 21000 | <2 |
| Example 15-2 | 17 | 6.5 | <2 | 20000 | 2.3 | <2 | 17000 | <2 |
| Example 16 | 16 | 630 | 30 | 27000 | 120 | 4.0 | 9900 | <2 |
| Example 17 | 25 | 57 | 6.0 | 13000 | 7.8 | <2 | 19000 | <2 |
| Comparative Example 3 | 76 | 2700 | 55 | 20000 | 990 | 6 | 2700 | 5 |

(n = mean of 2)

Ba, Co, Cr, Cu, Li, Ni, Pb, Sn are <2

Example 18: Preparation Method of Divalent Cation-Removed DAG (Sodium Type Cation Exchange Resin, Batch Type Dialysis Treatment)

Deacylated gellan gum (KELCOGEL CG-LA, manufactured by SANSHO Co., Ltd.) (300 mg), ultrapure water (Milli-Q water) (30 mL), and Duolite C467 (0.5 g) were added, and the mixture was dissolved by stirring with heating at 70° C. for 1 hr. The mixture was allowed to cool to room temperature, and Duolite C467 was removed by suction filtration. The filtrate was dialyzed against water for one day. The obtained aqueous solution was freeze-dried to give a white solid (187 mg).

Example 19: Production of DMEM Medium Using Divalent Cation-Removed Deacylated Gellan Gum (Filter Sterilization)

Divalent cation-removed deacylated gellan gum prepared in Example 18 was added to water at 0.3%, and the mixture was dispersed by heating at 100° C. Then, the mixture was stood at room temperature. The solution was sterilized with a sterilization filter (pore size 0.22 μm).

On the other hand, to a powder medium of DMEM/F12 (Siyma-Aldrich Co. LLC.) and sodium hydrogen carbonate was added pure water in an amount of one-second of the recommended level on preparation of the medium, and the mixture was sterilized with a sterilization filter (pore size 0.22 μm).

Deacylated gellan gum solution, Milli-Q water and the medium were mixed at a volume ratio of 1:9:10, whereby the object DMEM/F12 medium having a deacylated gellan gum concentration of 0.015% (w/v) was prepared.

Example 20: Production of DMEM Medium Using Divalent Cation-Removed Deacylated Gellan Gum (Autoclave Sterilization)

Divalent cation-removed deacylated gellan gum prepared in Example 18 was added to water at 0.3%, and the mixture was dispersed by heating at 100° C. Then, the mixture was stood at room temperature. The obtained solution was sterilized in an autoclave at 121° C. for 20 min.

On the other hand, to a powder medium of DMEM/F12 (Sigma-Aldrich Co. LLC.) and sodium hydrogen carbonate was added pure water in an amount of one-second of the recommended level on preparation of the medium, and the mixture was sterilized with a sterilization filter (pore size 0.22 μm).

Deacylated gellan gum solution, Milli-Q water and the sterilized medium were mixed at a volume ratio of 1:9:10, whereby the object DMEM/F12 medium having a deacylated gellan gum concentration of 0.015% (w/v) was prepared.

Example 21: Bead Dispersion Test

Polystyrene beads (size 200 μm, manufactured by Polysciences Inc.) were added to the medium prepared in Examples 19 and 20, and the dispersion state of the beads was confirmed by visual observation. For evaluation, a suspended and dispersed state is ○, partial sedimentation/dispersed state is Δ, and sedimented state is x.

TABLE 50

| Example | bead dispersion |
|---|---|
| Example 19 | ○ |
| Example 20 | ○ |

INDUSTRIAL APPLICABILITY

The present invention provides a production method of a medium composition comprising a polymer compound having an anionic functional group, which increases solubility of the polymer compound in water, and affords more convenient mixing of the aforementioned compound and the medium. Since the method permits convenient production of a medium composition capable of suspension culture of cells and/or tissues, the present invention is an industrially extremely useful invention.

The contents disclosed in any publication cited herein, including patents and patent applications, are hereby incorporated in their entireties by reference, to the extent that they have been disclosed herein.

This application is based on patent application Nos. 2014-010841 (filing date: Jan. 23, 2014) and 2014-170992 (filing date: Aug. 25, 2014), filed in Japan, the contents of which are incorporated in full herein.

The invention claimed is:

1. A method of producing a liquid medium composition capable of suspension culture of cells or tissues, comprising:
    (a) subjecting deacylated gellan gum or a salt thereof to a divalent cation removal treatment;
    (b) dissolving the deacylated gellan gum or a salt thereof subjected to the divalent cation removal treatment in water, without heating, to provide an aqueous solution at a concentration at which the deacylated gellan gum or a salt thereof before the divalent cation removal treatment is insoluble in water at room temperature;
    (c) providing an aqueous solution of a culture medium; and
    (d) mixing the aqueous solution of deacylated gellan gum or a salt thereof and the aqueous solution of a culture medium,
    thereby producing the liquid medium composition capable of suspension culture of cells or tissues.

2. The production method of claim 1, wherein the divalent metal cation removal treatment is performed by mixing a suspension of the deacylated gellan gum or a salt thereof in water and a cation exchanger.

3. The production method of claim 2, wherein the suspension of the deacylated gellan gum or a salt thereof in water is mixed with the cation exchanger at 10-70° C.

4. The production method of claim 1, wherein the divalent metal cation is at least one kind selected from the group consisting of calcium ion, magnesium ion, zinc ion, iron ion and copper ion.

5. The production method of claim 1, wherein each aqueous solution is sterilized by filtration before mixing.

6. The production method of claim 1, wherein the aqueous solution of the deacylated gellan gum or a salt thereof is sterilized in an autoclave.

7. The production method of claim 1, wherein the aqueous solution of the deacylated gellan gum or a salt thereof and the aqueous solution of the culture medium are mixed with stirring.

8. The production method of claim 1, comprising mixing with stirring in a homomixer.

9. The production method of claim 1, wherein the divalent metal cation removal treatment is performed using a chelating agent.

10. The production method of claim 9, wherein the chelating agent is ethylenediaminetetraacetic acid.

11. The production method of claim 1, wherein the divalent metal cation removal treatment is performed using a cation exchanger.

12. The production method of claim 11, wherein the cation exchanger is of a sodium type.

13. A method of producing a liquid medium composition capable of suspension culture of cells or tissues, comprising:
- sterilizing by filtration an aqueous solution of deacylated gellan gum or a salt thereof, which has been subjected to a divalent cation removal treatment;
- sterilizing by filtration an aqueous solution of a culture medium; and
- mixing the sterilized aqueous solution of deacylated gellan gum or a salt thereof and the sterilized aqueous solution of a culture medium;
- thereby producing the liquid medium composition capable of suspension culture of cells or tissues.

* * * * *